(12) United States Patent
Bishop et al.

(10) Patent No.: US 8,845,962 B2
(45) Date of Patent: Sep. 30, 2014

(54) APPARATUS AND METHOD FOR STEAM DISINFECTION OF A POWDER

(75) Inventors: Michael Bishop, Dallas, TX (US); John LaBonte, Denison, TX (US); Joseph F. McCoy, Sherman, TX (US); Steven F. Schnittger, Huntington, NY (US)

(73) Assignee: ActiTech, L.P., Lewisville, TX (US)

( * ) Notice: Subject to any disclaimer, the term of this patent is extended or adjusted under 35 U.S.C. 154(b) by 0 days.

(21) Appl. No.: 13/489,994

(22) Filed: Jun. 6, 2012

(65) Prior Publication Data

US 2013/0001464 A1    Jan. 3, 2013

Related U.S. Application Data

(60) Provisional application No. 61/494,013, filed on Jun. 7, 2011.

(51) Int. Cl.
*A61L 2/07* (2006.01)

(52) U.S. Cl.
CPC ........................................ *A61L 2/07* (2013.01)
USPC .......................................................... 422/26

(58) Field of Classification Search
USPC .......................................................... 422/26
See application file for complete search history.

(56) References Cited

U.S. PATENT DOCUMENTS

| | | | | |
|---|---|---|---|---|
| 5,842,326 A | * | 12/1998 | Wolf | 53/425 |
| 6,912,800 B2 | * | 7/2005 | Vetter et al. | 34/380 |
| 7,699,811 B2 | * | 4/2010 | Hasegawa | 604/191 |
| 7,858,028 B2 | | 12/2010 | Adams | |
| 7,892,483 B2 | | 2/2011 | Amar et al. | |
| 7,895,938 B2 | | 3/2011 | Chang et al. | |
| 8,153,169 B1 | * | 4/2012 | Sepahvand | 424/725 |
| 2006/0177342 A1 | | 8/2006 | Bauer | |

FOREIGN PATENT DOCUMENTS

| | | |
|---|---|---|
| EP | 1452186 A1 | 9/2004 |
| EP | 1683469 A2 | 7/2006 |
| JP | 05-004678 A | 1/1993 |
| WO | 8102108 A1 | 8/1981 |
| WO | 2012/170540 A2 | 12/2012 |

OTHER PUBLICATIONS

International Search Report and Written Opinion for PCT/US2012/041111 dated Feb. 1, 2013.

* cited by examiner

*Primary Examiner* — Sean E Conley
(74) *Attorney, Agent, or Firm* — Chainey P. Singleton; Edwin S. Flores; Chalker Flores, LLP

(57) ABSTRACT

The present invention provides a system for the sterilization of natural products without negatively effecting the properties of the system having a sterilization chamber; a sample area within the sterilization chamber to hold one or more steam permeable containers; a heater source connected to the sterilization chamber for heating the sterilization chamber to a predetermined temperature; a heater control unit connected to the heater source for controlling the predetermined temperature; a pressure source connected to the sterilization chamber for pressurizing the sterilization chamber to a predetermined pressure; a pressure control unit connected to the pressure source for controlling the predetermined pressure; a steam aperture for supplying steam to the sterilization chamber; a steam control unit connected to the temperature and duration of the steam; and an interface connected to the heater control unit, pressure control unit, and steam control unit.

8 Claims, 30 Drawing Sheets

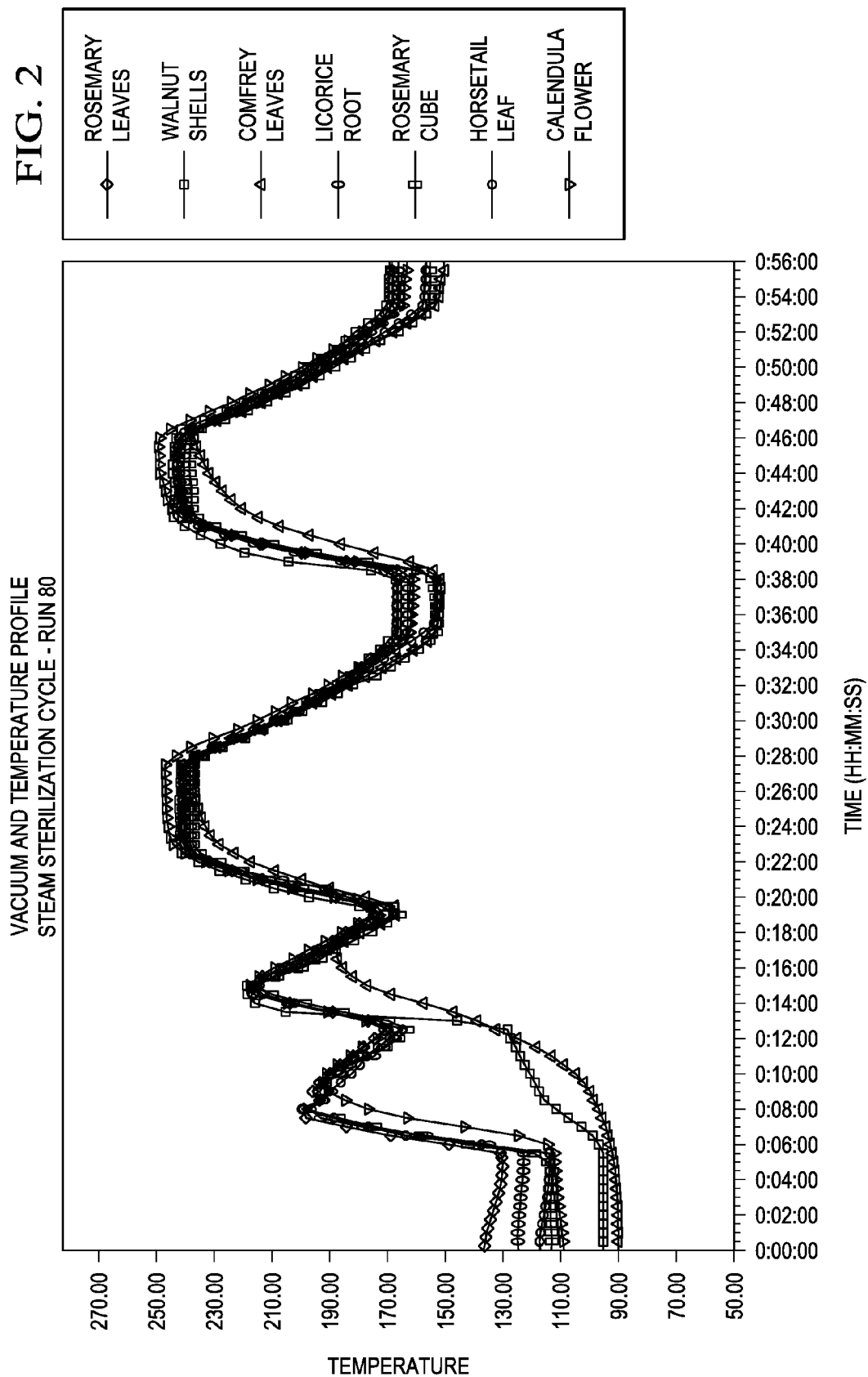

FIG. 4

ActiPure™ - RUN # C154 12/02/10

| BAG # | PRODUCT | INITIAL WEIGHT | AFTER ActiPure™ WEIGHT | WEIGHT DIFFERENCE | % LOSS |
|---|---|---|---|---|---|
| 8 | CINNAMON CASSIA POWDER | 24.60 | 23.54 | (1.06) | -4% |
| 9 | CINNAMON CASSIA POWDER | 23.60 | 22.52 | (1.08) | -5% |
| 10 | CINNAMON CASSIA POWDER | 25.00 | 23.86 | (1.14) | -5% |
| 11 | CINNAMON CASSIA POWDER | 24.69 | 23.54 | (1.15) | -5% |
| 12 | CINNAMON CASSIA POWDER | 24.71 | 23.70 | (1.01) | -4% |
| 13 | CINNAMON CASSIA POWDER | 24.60 | 23.58 | (1.02) | -4% |
| 14 | CINNAMON CASSIA POWDER | 25.00 | 23.52 | (1.48) | -6% |
| 15 | CINNAMON CASSIA POWDER | 25.00 | 23.88 | (1.12) | -4% |
| 16 | CINNAMON CASSIA POWDER | 25.00 | 24.04 | (0.96) | -4% |
| 17 | CINNAMON CASSIA POWDER | 25.00 | 24.10 | (0.90) | -4% |
| 18 | CINNAMON CASSIA POWDER | 24.66 | 23.68 | (0.98) | -4% |
| 19 | CINNAMON CASSIA POWDER | 24.42 | 23.54 | (0.88) | -4% |
| 20 | CINNAMON CASSIA POWDER | 25.00 | 24.06 | (0.94) | -4% |
| 21 | CINNAMON CASSIA POWDER | 25.00 | 24.04 | (0.96) | -4% |
| 22 | CINNAMON CASSIA POWDER | 25.00 | 24.08 | (0.92) | -4% |
| 23 | CINNAMON CASSIA POWDER | 25.00 | 24.16 | (0.84) | -3% |
| 24 | CINNAMON CASSIA POWDER | 25.00 | 23.72 | (1.28) | -5% |
| 25 | CINNAMON CASSIA POWDER | 25.00 | 24.12 | (0.88) | -4% |
| 26 | CINNAMON CASSIA POWDER | 24.52 | 23.30 | (1.22) | -5% |
| 27 | CINNAMON CASSIA POWDER | 25.00 | 24.08 | (0.92) | -4% |
| 28 | CINNAMON CASSIA POWDER | 25.00 | 24.00 | (1.00) | -4% |
| 29 | CINNAMON CASSIA POWDER | 25.00 | 24.12 | (0.88) | -4% |
| 30 | CINNAMON CASSIA POWDER | 25.00 | 24.00 | (1.00) | -4% |
| 36 | CINNAMON CASSIA POWDER | 24.60 | 23.46 | (1.14) | -5% |
| 37 | CINNAMON CASSIA POWDER | 25.00 | 23.92 | (1.08) | -4% |
| 38 | CINNAMON CASSIA POWDER | 24.59 | 24.06 | (0.53) | -2% |
| 39 | CINNAMON CASSIA POWDER | 25.00 | 23.60 | (1.40) | -6% |
| 40 | CINNAMON CASSIA POWDER | 24.50 | 23.54 | (0.96) | -4% |
| 41 | CINNAMON CASSIA POWDER | 25.00 | 24.06 | (0.94) | -4% |
| 42 | CINNAMON CASSIA POWDER | 24.59 | 23.64 | (0.95) | -4% |
| 43 | CINNAMON CASSIA POWDER | 24.68 | 23.62 | (1.06) | -4% |
| 44 | CINNAMON CASSIA POWDER | 25.00 | 23.56 | (1.44) | -6% |
| 45 | CINNAMON CASSIA POWDER | 24.55 | 23.64 | (0.91) | -4% |
| 46 | CINNAMON CASSIA POWDER | 24.80 | 23.74 | (1.06) | -4% |
| 47 | CINNAMON CASSIA POWDER | 23.82 | 22.84 | (0.98) | -4% |
| 48 | CINNAMON CASSIA POWDER | 25.00 | 24.08 | (0.92) | -4% |
| | TOTALS: | 891.93 | 854.94 | (36.99) | -4% |
| | AVERAGE % LOSS: | | | | -4% |

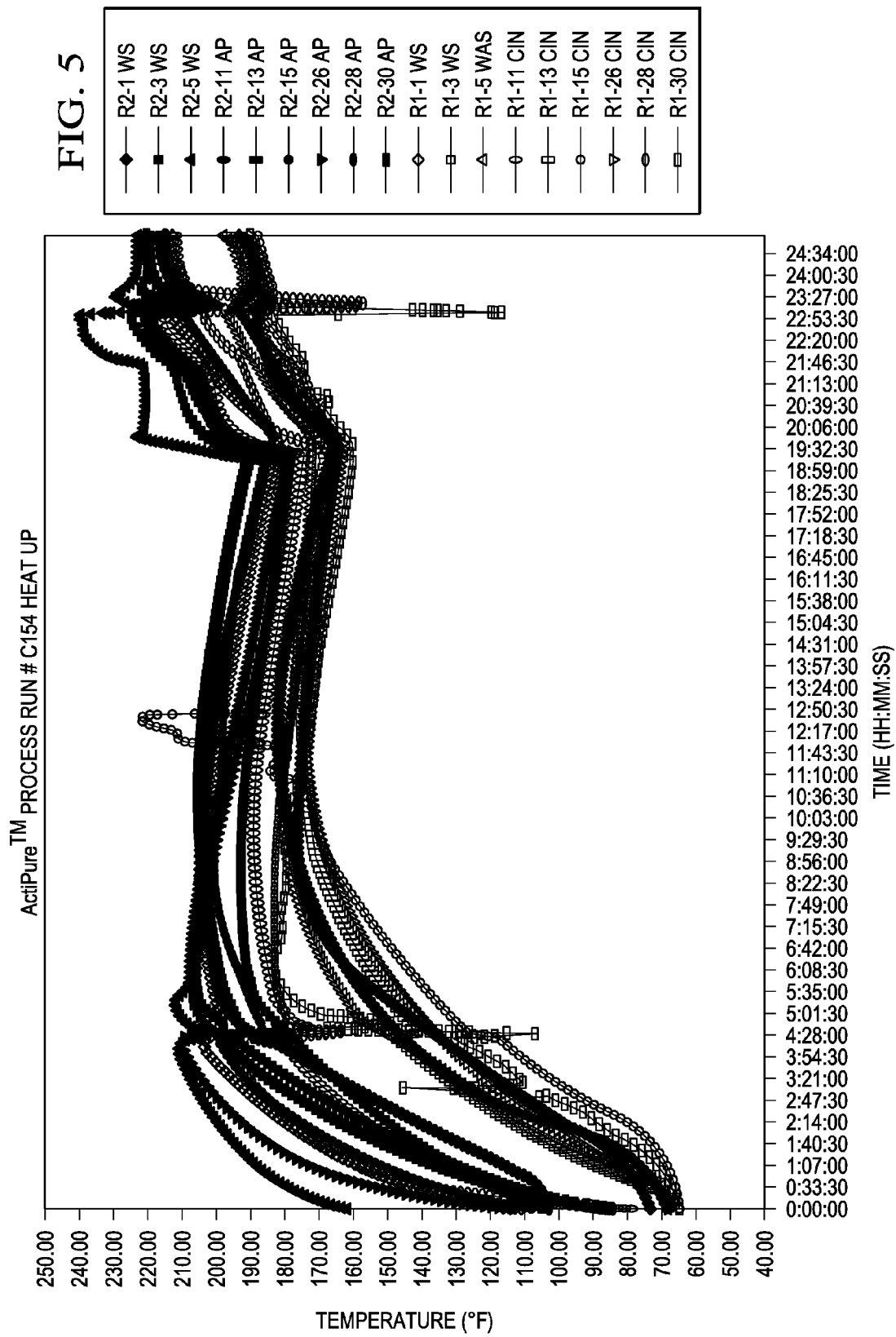

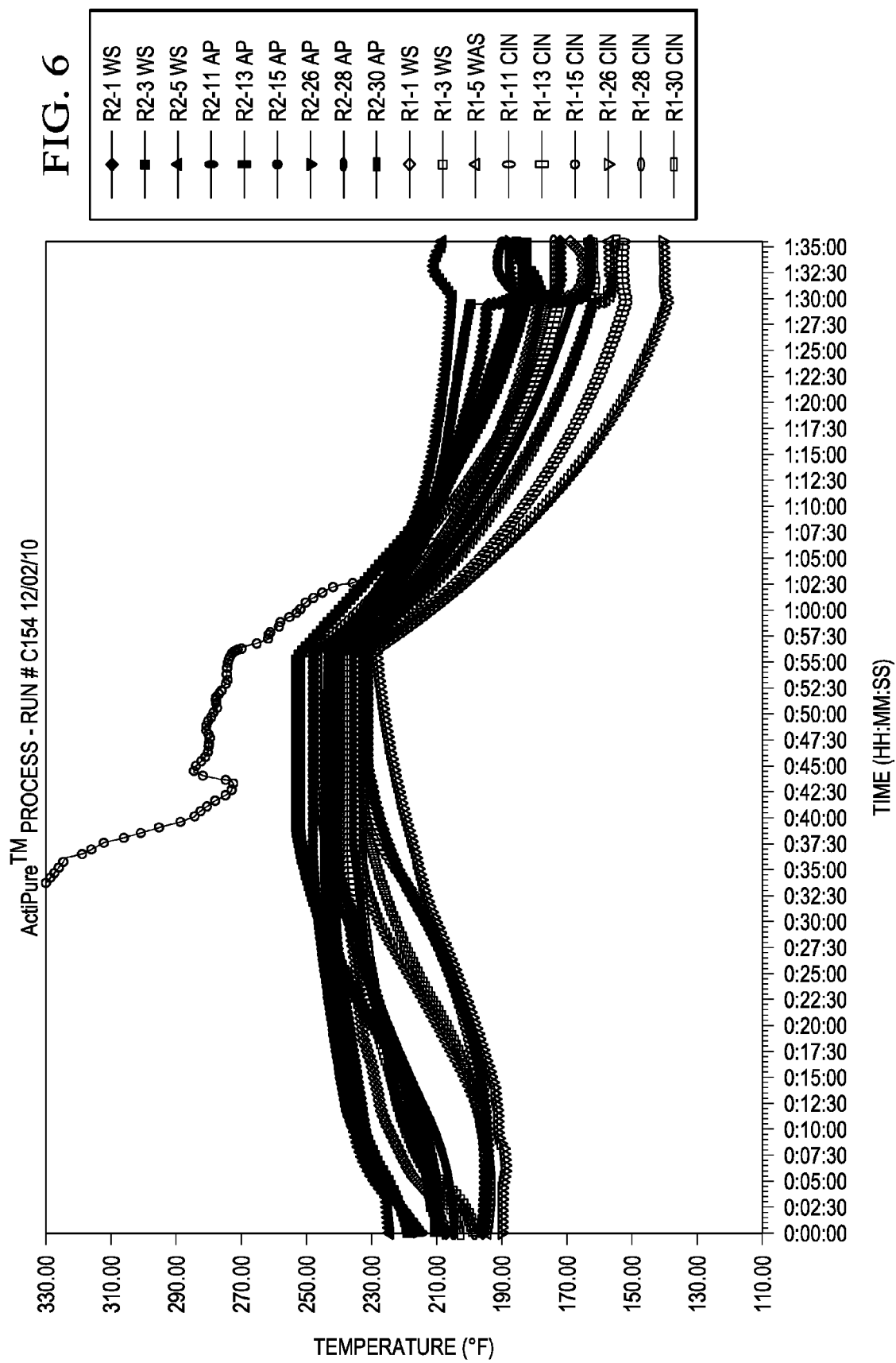

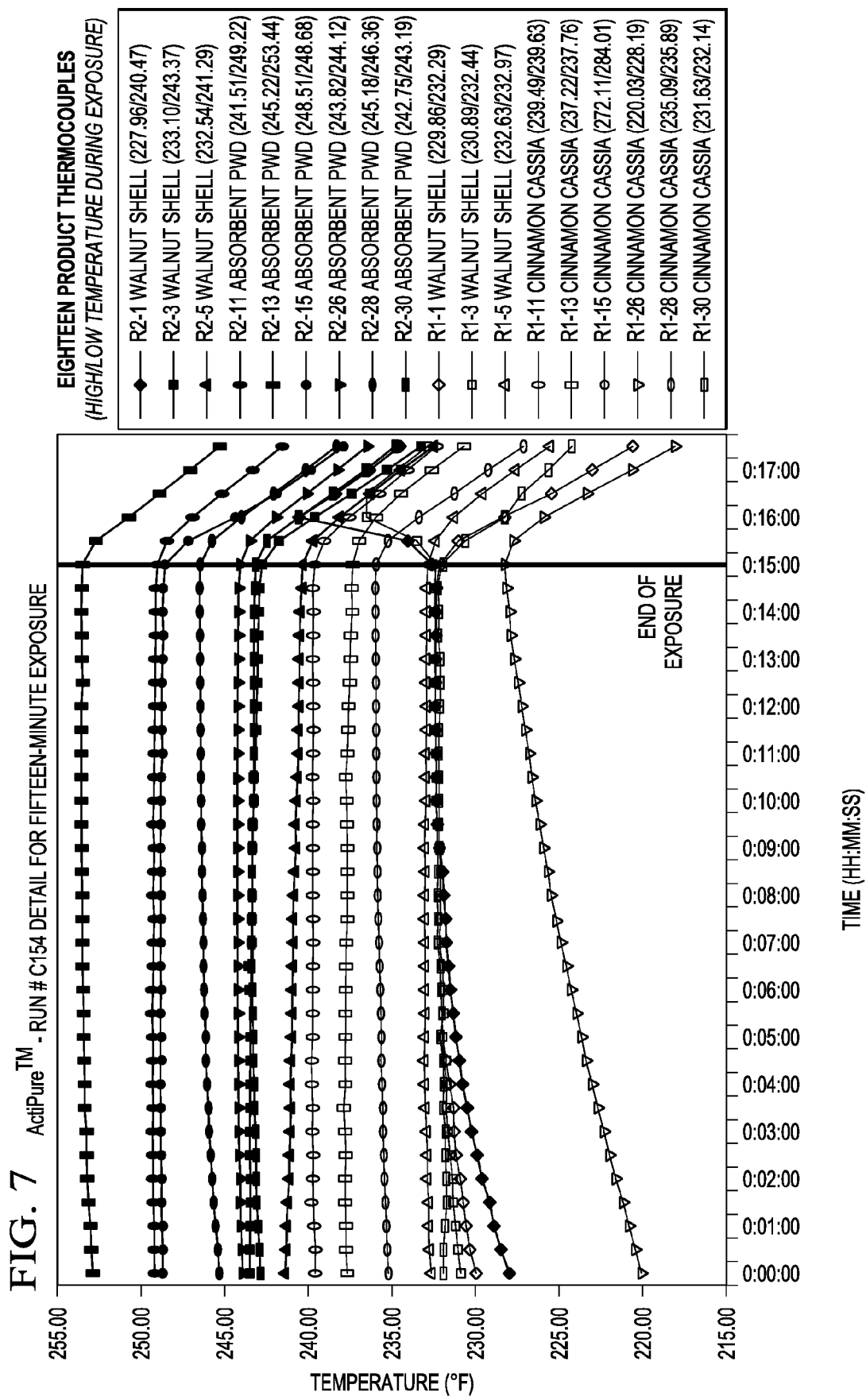

| CART 1 | | INITIAL MICRO | | POST ActiPure™ MICRO | | | ALL SAMPLES | LOG REDUCTION |
|---|---|---|---|---|---|---|---|---|
| | | APC | YEAST/MOLD | SAMPLE 1 APC | SAMPLE 2 APC | SAMPLE 3 APC | YEAST/MOLD | |
| BAG 1 | WALNUT SHELL POWDER | N/A | N/A | <10 | <10 | <10 | <10 | N/A |
| BAG 3 | WALNUT SHELL POWDER | N/A | N/A | <10 | <10 | <10 | <10 | N/A |
| BAG 5 | WALNUT SHELL POWDER | N/A | N/A | <10 | <10 | <10 | <10 | N/A |
| BAG 11 | CINNAMON CASSIA POWDER | 77,000 | <10 | <10 | <10 | <10 | <10 | 5 |
| BAG 13 | CINNAMON CASSIA POWDER | 77,000 | <10 | <10 | <10 | <10 | <10 | 5 |
| BAG 15 | CINNAMON CASSIA POWDER | 77,000 | <10 | <10 | <10 | <10 | <10 | 5 |
| BAG 26 | CINNAMON CASSIA POWDER | 77,000 | <10 | <10 | <10 | <10 | <10 | 5 |
| BAG 28 | CINNAMON CASSIA POWDER | 77,000 | <10 | <10 | <10 | <10 | <10 | 5 |
| BAG 30 | CINNAMON CASSIA POWDER | 77,000 | <10 | <10 | <10 | <10 | <10 | 5 |

FIG. 8A

| CART 2 | | INITIAL MICRO | | POST ActiPure™ MICRO | | | | LOG REDUCTION |
|---|---|---|---|---|---|---|---|---|
| | | | | SAMPLE 1 | SAMPLE 2 | SAMPLE 3 | ALL SAMPLES | |
| | | APC | YEAST/MOLD | APC | APC | APC | YEAST/MOLD | |
| BAG 1 | WALNUT SHELL POWDER | N/A | N/A | <10 | <10 | <10 | <10 | N/A |
| BAG 3 | WALNUT SHELL POWDER | N/A | N/A | <10 | <10 | <10 | <10 | N/A |
| BAG 5 | WALNUT SHELL POWDER | N/A | N/A | <10 | <10 | <10 | <10 | N/A |
| BAG 11 | ABSORBENT POWDER | N/A | N/A | <10 | <10 | <10 | <10 | N/A |
| BAG 13 | ABSORBENT POWDER | N/A | N/A | <10 | <10 | <10 | <10 | N/A |
| BAG 15 | ABSORBENT POWDER | N/A | N/A | <10 | <10 | <10 | <10 | N/A |
| BAG 26 | ABSORBENT POWDER | N/A | N/A | <10 | <10 | <10 | <10 | N/A |
| BAG 28 | ABSORBENT POWDER | N/A | N/A | <10 | <10 | <10 | <10 | N/A |
| BAG 30 | ABSORBENT POWDER | N/A | N/A | <10 | <10 | <10 | <10 | N/A |

FIG. 8B

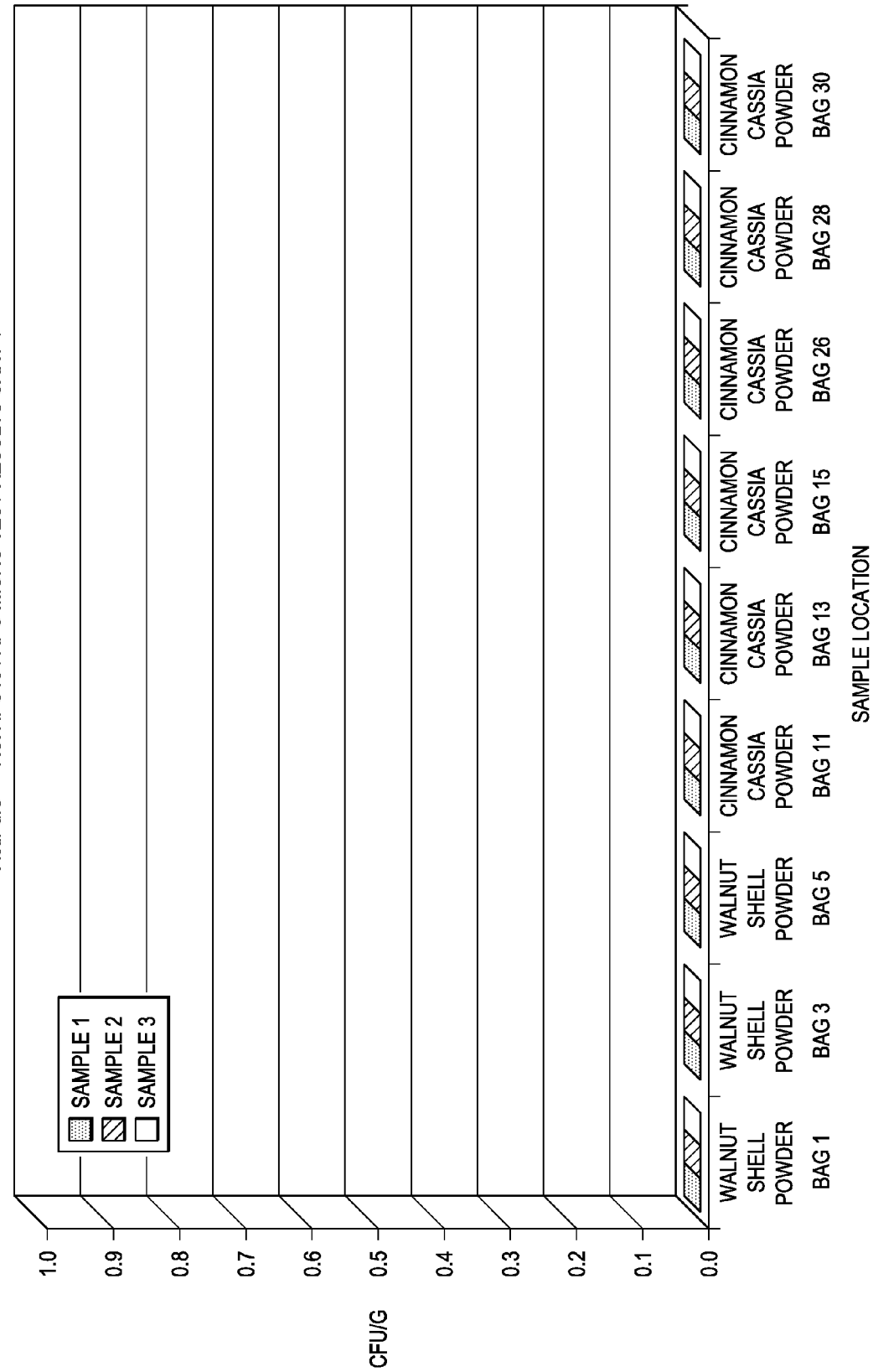

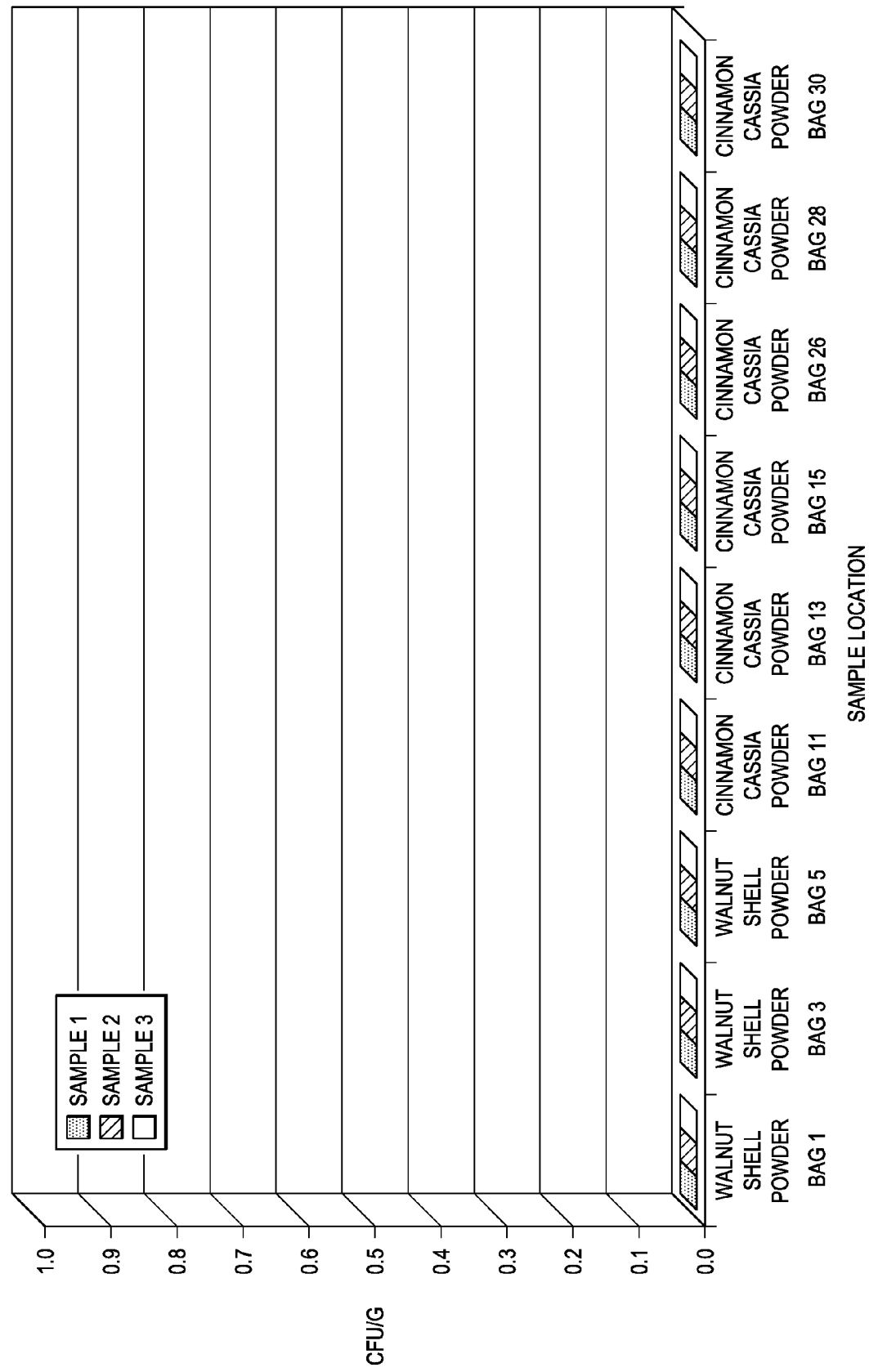

FIG. 12

CART # 1
RUN # C174     RUN # C174 % LOSS

| | PRODUCT | LOT # | PRE-BAG WEIGHT | POST BAG WEIGHT |
|---|---|---|---|---|
| 1 | NONI FRUIT POWDER | SBJ-S010157 | 25.4 | 24.4 |
| 2 | NONI FRUIT POWDER | SBJ-S010157 | 25.6 | 24.6 |
| 3 | NONI FRUIT POWDER | SBJ-S010157 | 25.5 | 24.6 |
| 4 | NONI FRUIT POWDER | SBJ-S010157 | 25.4 | 24.3 |
| 5 | NONI FRUIT POWDER | SBJ-S010157 | 25.6 | 24.6 |
| 6 | NONI FRUIT POWDER | SBJ-S010157 | 25.9 | 24.9 |
| 7 | NONI FRUIT POWDER | SBJ-S010157 | 25.7 | 24.6 |
| 8 | NONI FRUIT POWDER | SBJ-S010157 | 25.5 | 24.5 |
| 9 | NONI FRUIT POWDER | SBJ-S010157 | 25.4 | 25.0 |
| 10 | NONI FRUIT POWDER | SBJ-S010157 | 25.8 | 24.8 |
| 11 | MANGOSTEEN FRUIT POWDER | SBI-S091538 | 25.0 | 24.5 |
| 12 | MANGOSTEEN FRUIT POWDER | SBI-S091538 | 19.2 | 18.6 |
| 13 | NONI FRUIT POWDER | SBJ-S010151 | 25.3 | 24.3 |
| 14 | NONI FRUIT POWDER | SBJ-S010151 | 25.6 | 24.6 |
| 15 | NONI FRUIT POWDER | SBJ-S010151 | 25.4 | 24.5 |
| 16 | MUIRA PUAMA BARK POWDER | SBJ-S071107 | 25.8 | 25.5 |
| 17 | MUIRA PUAMA BARK POWDER | SBJ-S071107 | 25.4 | 25.1 |
| 18 | MUIRA PUAMA BARK POWDER | SBJ-S071107 | 25.6 | 25.5 |
| 19 | MUIRA PUAMA BARK POWDER | SBJ-S071107 | 25.6 | 25.5 |
| 20 | MUIRA PUAMA BARK POWDER | SBJ-S071107 | 25.4 | 25.1 |
| 21 | MUIRA PUAMA BARK POWDER | SBJ-S071107 | 25.8 | 25.5 |
| 22 | MUIRA PUAMA BARK POWDER | SBJ-S071107 | 25.5 | 25.2 |
| 23 | MUIRA PUAMA BARK POWDER | SBJ-S071107 | 25.4 | 25.1 |
| 24 | MUIRA PUAMA BARK POWDER | SBJ-S071107 | 25.5 | 25.3 |
| 25 | MUIRA PUAMA BARK POWDER | SBJ-S071107 | 25.6 | 25.3 |
| 26 | NONI FRUIT POWDER | SBI-S010151 | 7.3 | 6.9 |
| 27 | NONI FRUIT POWDER | SBI-S010151 | 25.5 | 25.4 |
| 28 | MUIRA PUAMA BARK POWDER | SBJ-S071107 | 25.5 | 25.6 |
| 29 | MUIRA PUAMA BARK POWDER | SBJ-S071107 | 25.5 | 26.2 |
| 30 | MUIRA PUAMA BARK POWDER | SBJ-S071107 | 25.4 | 25.2 |
| 31 | NONI FRUIT POWDER | SBJ-S010151 | 25.7 | 24.7 |
| 32 | NONI FRUIT POWDER | SBJ-S010151 | 25.3 | 24.3 |
| 33 | NONI FRUIT POWDER | SBJ-S010151 | 25.4 | 24.4 |
| 34 | ASTRAGALUS ROOT POWDER | SBI-S060914 | 25.5 | 24.6 |
| 35 | ASTRAGALUS ROOT POWDER | SBI-S060914 | 25.8 | 24.9 |
| 36 | ASTRAGALUS ROOT POWDER | SBI-S060914 | 25.4 | 24.6 |
| 37 | ASTRAGALUS ROOT POWDER | SBI-S060914 | 26.2 | 25.3 |
| 38 | ASTRAGALUS ROOT POWDER | SBI-S060914 | 25.8 | 25.0 |
| 39 | ASTRAGALUS ROOT POWDER | SBI-S060914 | 25.6 | 24.8 |
| 40 | ASTRAGALUS ROOT POWDER | SBI-S060914 | 25.8 | 25.0 |
| 41 | ASTRAGALUS ROOT POWDER | SBI-S060914 | 26.1 | 24.8 |
| 42 | ASTRAGALUS ROOT POWDER | SBI-S060914 | 25.6 | 25.2 |
| 43 | ASTRAGALUS ROOT POWDER | SBI-S060914 | 25.7 | 24.8 |
| 44 | ASTRAGALUS ROOT POWDER | SBI-S060914 | 25.5 | 24.6 |
| 45 | ASTRAGALUS ROOT POWDER | SBI-S060914 | 25.8 | 25.0 |
| 46 | NONI FRUIT POWDER | SBJ-S010151 | 25.6 | 24.7 |
| 47 | NONI FRUIT POWDER | SBJ-S010151 | 25.5 | 24.6 |
| 48 | ASTRAGALUS ROOT POWDER | SBI-S060914 | 25.6 | 24.8 |
| | | | 1203.0 | 1171.3 |

DIFFERENCE: -31.70
% LOSS: -3%

CART # 2
RUN # C174     RUN # C174 % LOSS

| | PRODUCT | LOT # | PRE-BAG WEIGHT | POST BAG WEIGHT |
|---|---|---|---|---|
| 1 | ASTRAGALUS ROOT POWDER | SBI-S060914 | 25.7 | 24.88 |
| 2 | ASTRAGALUS ROOT POWDER | SBI-S060914 | 25.5 | 24.7 |
| 3 | ASTRAGALUS ROOT POWDER | SBI-S060914 | 25.2 | 24.4 |
| 4 | ASTRAGALUS ROOT POWDER | SBI-S060914 | 25.7 | 24.88 |
| 5 | ASTRAGALUS ROOT POWDER | SBI-S060914 | 25.1 | 24.33 |
| 6 | ASTRAGALUS ROOT POWDER | SBI-S060914 | 25.1 | 24.3 |
| 7 | ASTRAGALUS ROOT POWDER | SBI-S060914 | 25.8 | 24.9 |
| 8 | ASTRAGALUS ROOT POWDER | SBI-S060914 | 25.7 | 24.9 |
| 9 | ASTRAGALUS ROOT POWDER | SBI-S060914 | 13.0 | 12.48 |
| 10 | ELEUTHERO ROOT POWDER | SBJ-S111734 | 25.7 | 25.0 |
| 11 | ELEUTHERO ROOT POWDER | SBJ-S111734 | 25.8 | 25.17 |
| 12 | ELEUTHERO ROOT POWDER | SBJ-S111734 | 25.3 | 25.0 |
| 13 | ELEUTHERO ROOT POWDER | SBJ-S111734 | 25.9 | 25.2 |
| 14 | ELEUTHERO ROOT POWDER | SBJ-S111734 | 25.7 | 25.1 |
| 15 | ELEUTHERO ROOT POWDER | SBJ-S111734 | 24.6 | 23.95 |
| 16 | ELEUTHERO ROOT POWDER | SBJ-S111734 | 25.8 | 25.1 |
| 17 | ELEUTHERO ROOT POWDER | SBJ-S111734 | 25.6 | 25.1 |
| 18 | ELEUTHERO ROOT POWDER | SBJ-S111734 | 24.8 | 25.1 |
| 19 | ELEUTHERO ROOT POWDER | SBJ-S111734 | 25.7 | 25.1 |
| 20 | ELEUTHERO ROOT POWDER | SBJ-S111734 | 25.8 | 25.2 |
| 21 | ELEUTHERO ROOT POWDER | SBJ-S111734 | 25.9 | 25.2 |
| 22 | ELEUTHERO ROOT POWDER | SBJ-S111734 | 25.7 | 25.0 |
| 23 | ELEUTHERO ROOT POWDER | SBJ-S111734 | 25.8 | 25.3 |
| 24 | ELEUTHERO ROOT POWDER | SBJ-S111734 | 25.7 | 25.1 |
| 25 | ELEUTHERO ROOT POWDER | SBJ-S111734 | 25.8 | 25.2 |
| 26 | ASTRAGALUS ROOT POWDER | SBI-S060914 | 25.9 | 25.2 |
| 27 | ASTRAGALUS ROOT POWDER | SBI-S060914 | 25.1 | 24.41 |
| 28 | ASTRAGALUS ROOT POWDER | SBI-S060914 | 25.2 | 24.5 |
| 29 | ASTRAGALUS ROOT POWDER | SBI-S060914 | 25.3 | 24.6 |
| 30 | ASTRAGALUS ROOT POWDER | SBI-S060914 | 25.8 | 25.0 |
| 31 | ASTRAGALUS ROOT POWDER | SBI-S060914 | 26.0 | 25.2 |
| 32 | ASTRAGALUS ROOT POWDER | SBI-S060914 | 25.8 | 25.0 |
| 33 | ASTRAGALUS ROOT POWDER | SBI-S060914 | 25.9 | 25.1 |
| 34 | ASTRAGALUS ROOT POWDER | SBI-S060914 | 25.1 | 24.3 |
| 35 | ASTRAGALUS ROOT POWDER | SBI-S060914 | 25.2 | 24.42 |
| 36 | ASTRAGALUS ROOT POWDER | SBI-S060914 | 25.6 | 24.8 |
| 37 | ELEUTHERO ROOT POWDER | SBJ-S111734 | 25.8 | 25.2 |
| 38 | ELEUTHERO ROOT POWDER | SBJ-S111734 | 25.8 | 25.1 |
| 39 | ELEUTHERO ROOT POWDER | SBJ-S111734 | 25.7 | 25.1 |
| 40 | ASTRAGALUS ROOT POWDER | SBI-S060914 | 25.7 | 25.0 |
| 41 | ELEUTHERO ROOT POWDER | SBJ-S111734 | 25.7 | 25.0 |
| 42 | ELEUTHERO ROOT POWDER | SBJ-S111734 | 25.7 | 25.0 |
| 43 | ASTRAGALUS ROOT POWDER | SBI-S060914 | 26.1 | 25.3 |
| 44 | ASTRAGALUS ROOT POWDER | SBI-S060914 | 26.0 | 25.1 |
| 45 | ASTRAGALUS ROOT POWDER | SBI-S060914 | 27.3 | 26.5 |
| 46 | ASTRAGALUS ROOT POWDER | SBI-S060914 | 25.0 | 24.2 |
| 47 | ASTRAGALUS ROOT POWDER | SBI-S060914 | 25.4 | 24.5 |
| 48 | ASTRAGALUS ROOT POWDER | SBI-S060914 | 25.1 | 24.4 |
| | | | 1216.6 | 1183.52 |

DIFFERENCE: -33.08
% LOSS: -3%

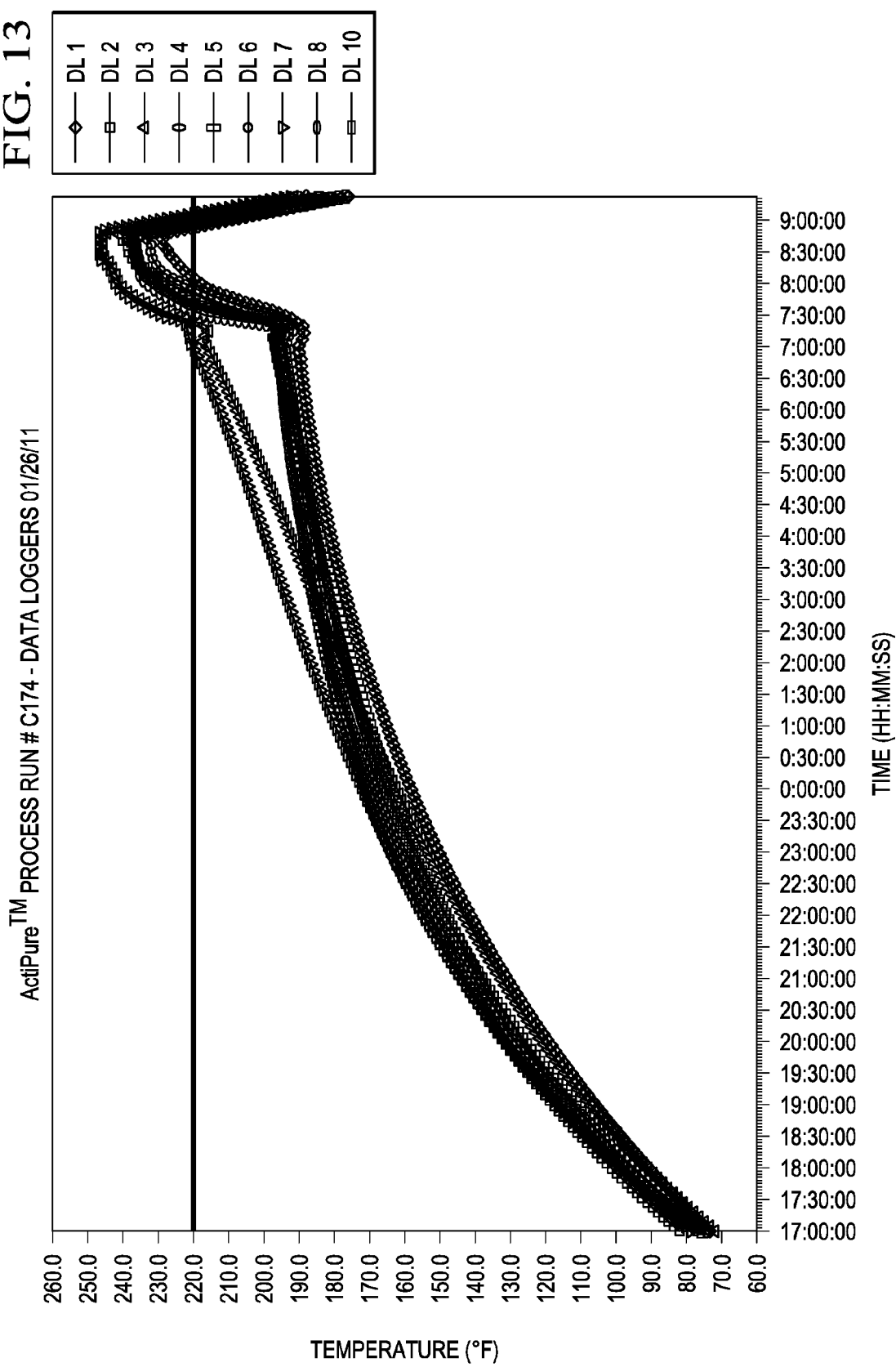

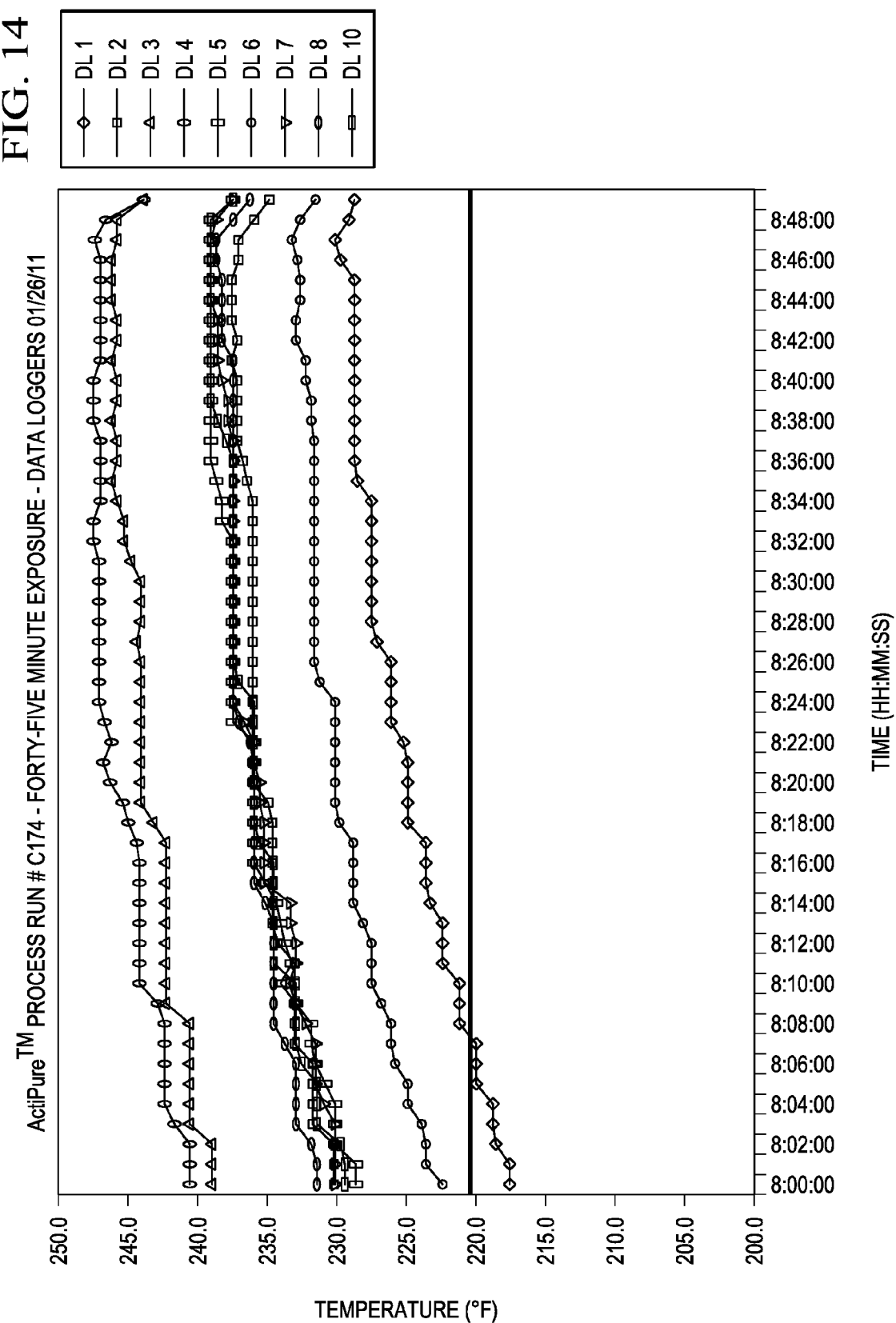

| CART 1 | | POST ActiPure™ MICRO | | | |
|---|---|---|---|---|---|
| | | SAMPLE 1 | SAMPLE 2 | SAMPLE 3 | ALL SAMPLES |
| | | APC | APC | APC | YEAST/ MOLD |
| BAG 5 | NONI FRUIT POWDER | <10 | <10 | <10 | <10 |
| BAG 15 | NONI FRUIT POWDER | <10 | <10 | <10 | <10 |
| BAG 30 | MUIRA PUAMA BARK POWDER | <10 | <10 | <10 | <10 |

|  | CART 2 | POST ActiPure™ MICRO | | | |
|---|---|---|---|---|---|
|  |  | SAMPLE 1 | SAMPLE 2 | SAMPLE 3 | ALL SAMPLES |
|  |  | APC | APC | APC | YEAST/ MOLD |
| BAG 1 | ASTRAGALUS ROOT POWDER | <10 | <10 | <10 | <10 |
| BAG 5 | ASTRAGALUS ROOT POWDER | <10 | <10 | <10 | <10 |
| BAG 11 | ELEUTHERO ROOT POWDER | <10 | <10 | <10 | <10 |
| BAG 15 | ELEUTHERO ROOT POWDER | <10 | <10 | <10 | <10 |
| BAG 26 | ASTRAGALUS ROOT POWDER | <10 | <10 | <10 | <10 |
| BAG 30 | ASTRAGALUS ROOT POWDER | <10 | <10 | <10 | <10 |

ActiPure™ - RUN # C156 12/7/10
CART 1 — WEIGHT LOSS DUE TO PROCESSING

| BAG # | PRODUCT | INITIAL WEIGHT | AFTER ActiPure™ WEIGHT | WEIGHT DIFFERENCE | % LOSS |
|---|---|---|---|---|---|
| 1 | CHAMOMILE POWDER | 17.00 | 15.70 | (1.30) | -8% |
| 2 | CHAMOMILE POWDER | 17.00 | 15.76 | (1.24) | -7% |
| 3 | CHAMOMILE POWDER | 17.00 | 15.82 | (1.18) | -7% |
| 4 | CHAMOMILE POWDER | 16.30 | 14.98 | (1.32) | -8% |
| 5 | CHAMOMILE POWDER | 17.00 | 15.82 | (1.18) | -7% |
| 6 | CHAMOMILE POWDER | 17.00 | 15.66 | (1.34) | -8% |
| 7 | CHAMOMILE POWDER | 17.00 | 15.90 | (1.10) | -6% |
| 8 | CHAMOMILE POWDER | 17.00 | 15.72 | (1.28) | -8% |
| 9 | CHAMOMILE POWDER | 16.50 | 15.26 | (1.24) | -8% |
| 10 | CHAMOMILE POWDER | 17.00 | 15.72 | (1.28) | -8% |
| 11 | CHAMOMILE POWDER | 16.50 | 15.10 | (1.40) | -8% |
| 12 | CHAMOMILE POWDER | 17.00 | 15.76 | (1.24) | -7% |
| 13 | CHAMOMILE POWDER | 17.00 | 15.74 | (1.26) | -7% |
| 14 | CHAMOMILE POWDER | 17.00 | 16.40 | (0.60) | -4% |
| 15 | CHAMOMILE POWDER | 17.00 | 15.76 | (1.24) | -7% |
| 16 | CHAMOMILE POWDER | 17.00 | 15.70 | (1.30) | -8% |
| 17 | CHAMOMILE POWDER | 17.00 | 15.76 | (1.24) | -7% |
| 18 | CHAMOMILE POWDER | 16.40 | 15.90 | (0.50) | -3% |
| 19 | DAMIANA POWDER | 25.00 | 23.52 | (1.48) | -6% |
| 20 | DAMIANA POWDER | 25.00 | 24.20 | (0.80) | -3% |
| 21 | CHAMOMILE POWDER | 17.00 | 15.80 | (1.20) | -7% |
| 22 | CHAMOMILE POWDER | 17.00 | 15.84 | (1.16) | -7% |
| 23 | CHAMOMILE POWDER | 17.00 | 15.84 | (1.16) | -7% |
| 24 | CHAMOMILE POWDER | 16.70 | 15.56 | (1.14) | -7% |
| 25 | CHAMOMILE POWDER | 17.00 | 15.76 | (1.24) | -7% |
| 26 | CHAMOMILE POWDER | 16.64 | 15.40 | (1.24) | -7% |
| 27 | CHAMOMILE POWDER | 17.00 | 15.54 | (1.46) | -9% |
| 28 | CHAMOMILE POWDER | 17.00 | 15.48 | (1.52) | -9% |
| 29 | CHAMOMILE POWDER | 16.50 | 15.36 | (1.14) | -7% |
| 30 | CHAMOMILE POWDER | 17.00 | 15.74 | (1.26) | -7% |
| 31 | CHAMOMILE POWDER | 17.00 | 15.90 | (1.10) | -6% |
| 32 | CHAMOMILE POWDER | 17.30 | 15.96 | (1.34) | -8% |
| 33 | CHAMOMILE POWDER | 15.50 | 14.40 | (1.10) | -7% |
| 34 | CHAMOMILE POWDER | 17.00 | 15.88 | (1.12) | -7% |
| 35 | CHAMOMILE POWDER | 17.00 | 15.76 | (1.24) | -7% |
| 36 | CHAMOMILE POWDER | 17.00 | 15.60 | (1.40) | -8% |
| 37 | CHAMOMILE POWDER | 16.50 | 15.28 | (1.22) | -7% |
| 38 | CHAMOMILE POWDER | 17.00 | 15.72 | (1.28) | -8% |
| 39 | CHAMOMILE POWDER | 16.50 | 15.16 | (1.34) | -8% |
| 40 | CHAMOMILE POWDER | 16.10 | 14.90 | (1.20) | -7% |
| 41 | CHAMOMILE POWDER | 17.08 | 15.90 | (1.18) | -7% |
| 42 | CHAMOMILE POWDER | 17.00 | 15.62 | (1.38) | -8% |
| 43 | CHAMOMILE POWDER | 17.00 | 15.68 | (1.32) | -8% |
| 44 | CHAMOMILE POWDER | 15.90 | 14.74 | (1.16) | -7% |
| 45 | CHAMOMILE POWDER | 16.30 | 14.96 | (1.34) | -8% |
| 46 | CHAMOMILE POWDER | 17.00 | 15.64 | (1.36) | -8% |
| 47 | CHAMOMILE POWDER | 16.30 | 15.18 | (1.12) | -7% |
| 48 | CHAMOMILE POWDER | 17.00 | 15.62 | (1.38) | -8% |
| | TOTALS: | 823.02 | 764.40 | (58.62) | -7% |
| | AVERAGE % LOSS: | | | | -7% |

FIG. 19

ActiPure™ - RUN # C156 12/7/10

CART 2 — WEIGHT LOSS DUE TO PROCESSING

| BAG # | PRODUCT | INITIAL WEIGHT | AFTER ActiPure™ WEIGHT | WEIGHT DIFFERENCE | % LOSS |
|---|---|---|---|---|---|
| 1 | CHAMOMILE POWDER | 17.06 | 15.84 | (1.22) | -7% |
| 2 | CHAMOMILE POWDER | 16.76 | 15.56 | (1.20) | -7% |
| 3 | CHAMOMILE POWDER | 17.09 | 15.97 | (1.12) | -7% |
| 4 | CHAMOMILE POWDER | 17.18 | 15.92 | (1.26) | -7% |
| 5 | CHAMOMILE POWDER | 17.12 | 15.92 | (1.20) | -7% |
| 6 | NOPAL POWDER | 25.00 | 24.02 | (0.98) | -4% |
| 7 | NOPAL POWDER | 25.00 | 23.84 | (1.16) | -5% |
| 8 | NOPAL POWDER | 25.00 | 23.82 | (1.18) | -5% |
| 9 | NOPAL POWDER | 25.50 | 25.14 | (0.36) | -1% |
| 10 | NOPAL POWDER | 25.00 | 24.22 | (0.78) | -3% |
| 11 | NOPAL POWDER | 25.00 | 24.08 | (0.92) | -4% |
| 12 | NOPAL POWDER | 25.00 | 22.76 | (2.24) | -9% |
| 13 | NOPAL POWDER | 25.00 | 23.90 | (1.10) | -4% |
| 14 | NOPAL POWDER | 25.00 | 24.08 | (0.92) | -4% |
| 15 | NOPAL POWDER | 25.00 | 24.12 | (0.88) | -4% |
| 16 | NOPAL POWDER | 25.00 | 24.04 | (0.96) | -4% |
| 17 | NOPAL POWDER | 25.00 | 23.94 | (1.06) | -4% |
| 18 | NOPAL POWDER | 25.00 | 24.04 | (0.96) | -4% |
| 19 | NOPAL POWDER | 25.00 | 22.86 | (2.14) | -9% |
| 20 | NOPAL POWDER | 25.00 | 23.96 | (1.04) | -4% |
| 21 | WILD YAM POWDER | 24.80 | 23.80 | (1.00) | -4% |
| 22 | WILD YAM POWDER | 24.80 | 23.62 | (1.18) | -5% |
| 23 | WILD YAM POWDER | 24.30 | 23.06 | (1.24) | -5% |
| 24 | WILD YAM POWDER | 25.00 | 24.00 | (1.00) | -4% |
| 25 | WILD YAM POWDER | 25.00 | 24.14 | (0.86) | -3% |
| 26 | DAMIANA POWDER | 24.00 | 22.78 | (1.22) | -5% |
| 27 | YUCCA ROOT POWDER | 24.00 | 23.76 | (0.24) | -1% |
| 28 | YUCCA ROOT POWDER | 24.00 | 22.80 | (1.20) | -5% |
| 29 | YUCCA ROOT POWDER | 24.00 | 23.92 | (0.08) | -0.3% |
| 30 | WILD YAM POWDER | 24.00 | 22.16 | (1.84) | -8% |
| 31 | CHAMOMILE POWDER | 16.00 | 15.08 | (0.92) | -6% |
| 32 | CHAMOMILE POWDER | 16.90 | 15.72 | (1.18) | -7% |
| 33 | CHAMOMILE POWDER | 16.30 | 15.00 | (1.30) | -8% |
| 34 | DAMIANA POWDER | 25.00 | 24.20 | (0.80) | -3% |
| 35 | DAMIANA POWDER | 25.00 | 24.10 | (0.90) | -4% |
| 36 | DAMIANA POWDER | 24.30 | 22.86 | (1.44) | -6% |
| 37 | NOPAL POWDER | 25.00 | 23.80 | (1.20) | -5% |
| 38 | NOPAL POWDER | 25.00 | 24.10 | (0.90) | -4% |
| 39 | NOPAL POWDER | 25.00 | 23.90 | (1.10) | -4% |
| 40 | YUCCA ROOT POWDER | 24.80 | 23.80 | (1.00) | -4% |
| 41 | YUCCA ROOT POWDER | 24.80 | 23.82 | (0.98) | -4% |
| 42 | YUCCA ROOT POWDER | 24.80 | 23.78 | (1.02) | -4% |
| 43 | ALOE VERA POWDER | 25.00 | 23.94 | (1.06) | -4% |
| 44 | ALOE VERA POWDER | 25.00 | 24.16 | (0.84) | -3% |
| 45 | ALOE VERA POWDER | 24.50 | 23.42 | (1.08) | -4% |
| 46 | ALOE VERA POWDER | 25.00 | 24.06 | (0.94) | -4% |
| 47 | ALOE VERA POWDER | 25.00 | 24.00 | (1.00) | -4% |
| 48 | ALOE VERA POWDER | 25.00 | 23.90 | (1.10) | -4% |
| | TOTALS: | 1127.01 | 1075.71 | (51.30) | -5% |
| | AVERAGE % LOSS: | | | | -5% |

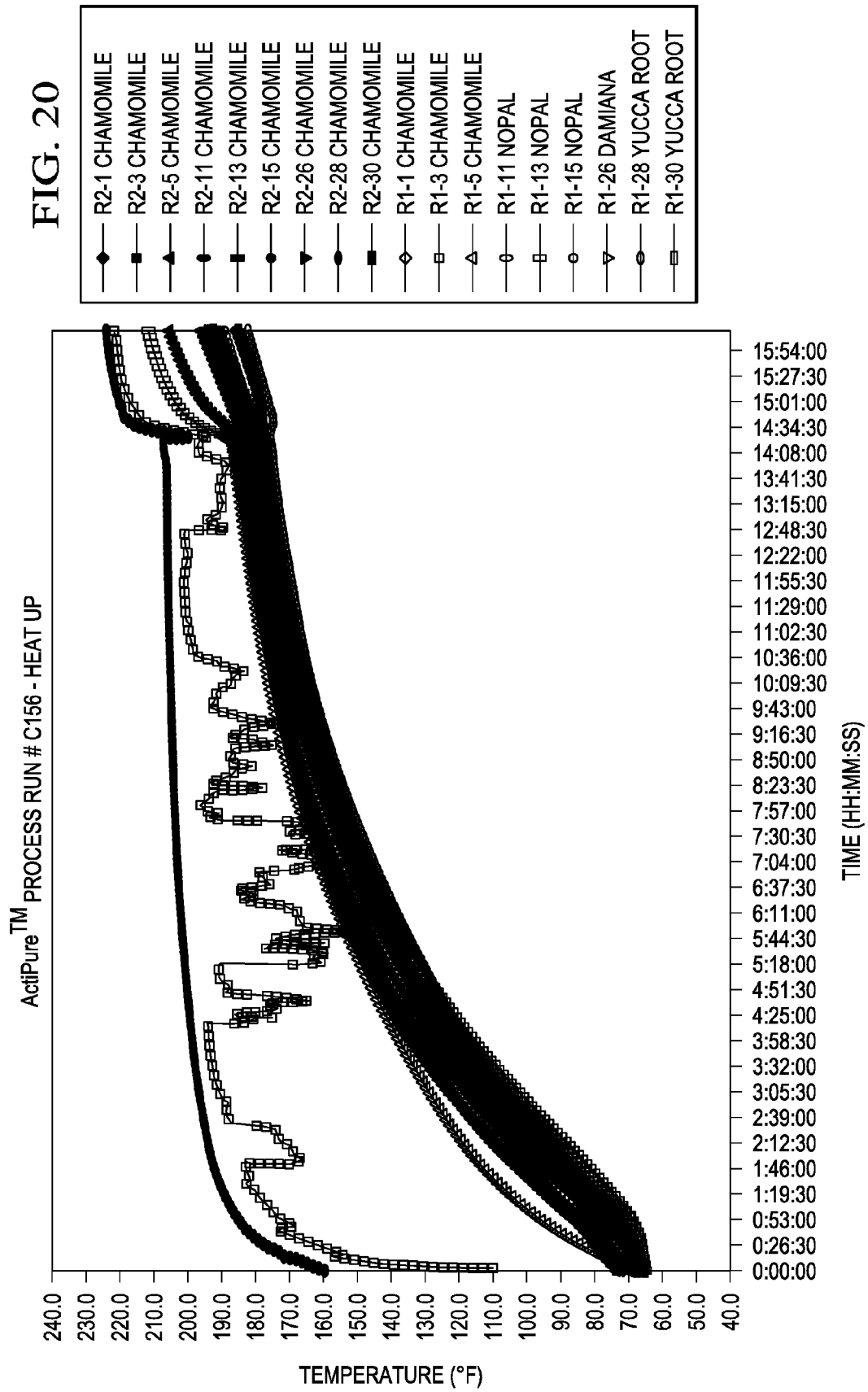

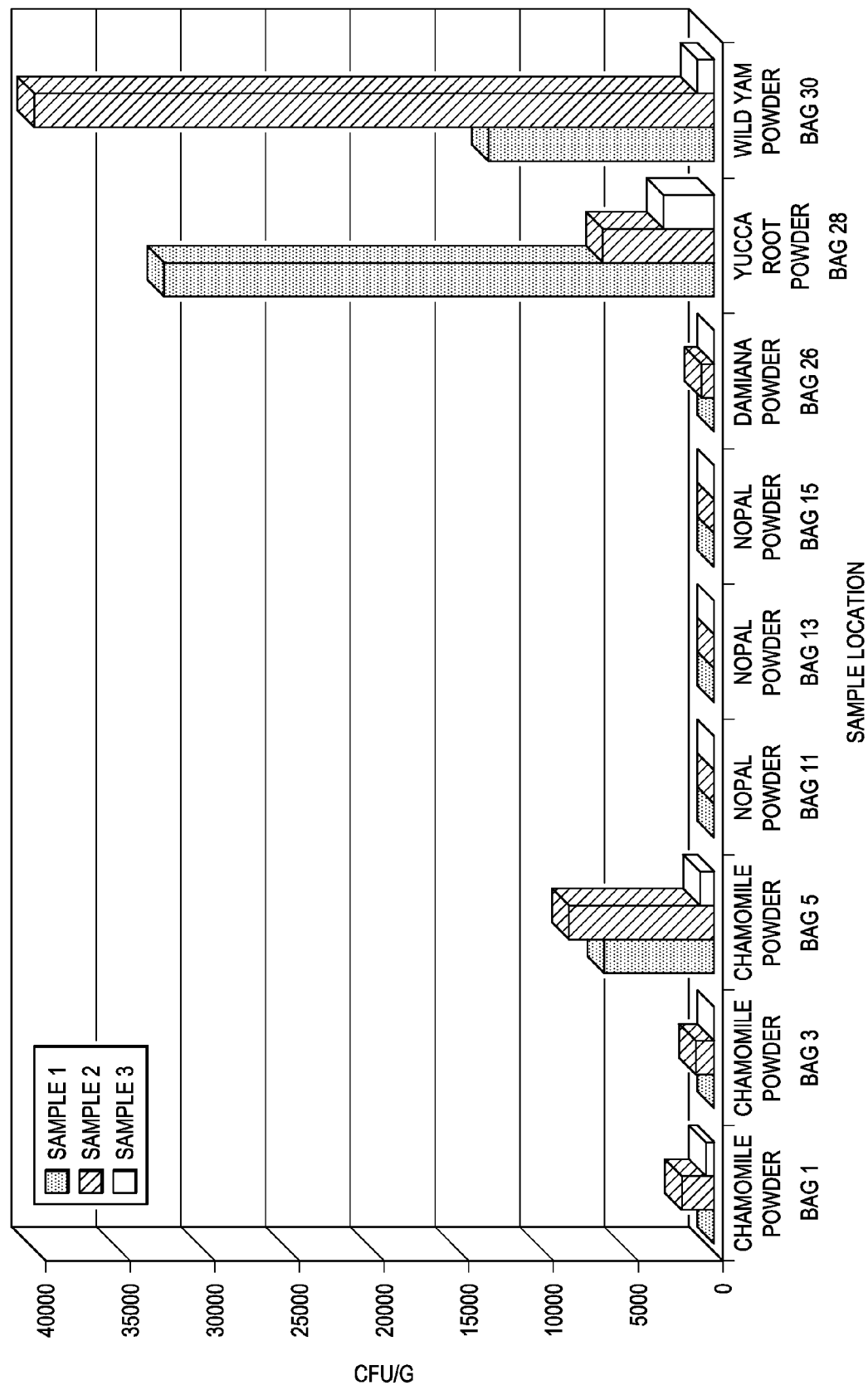

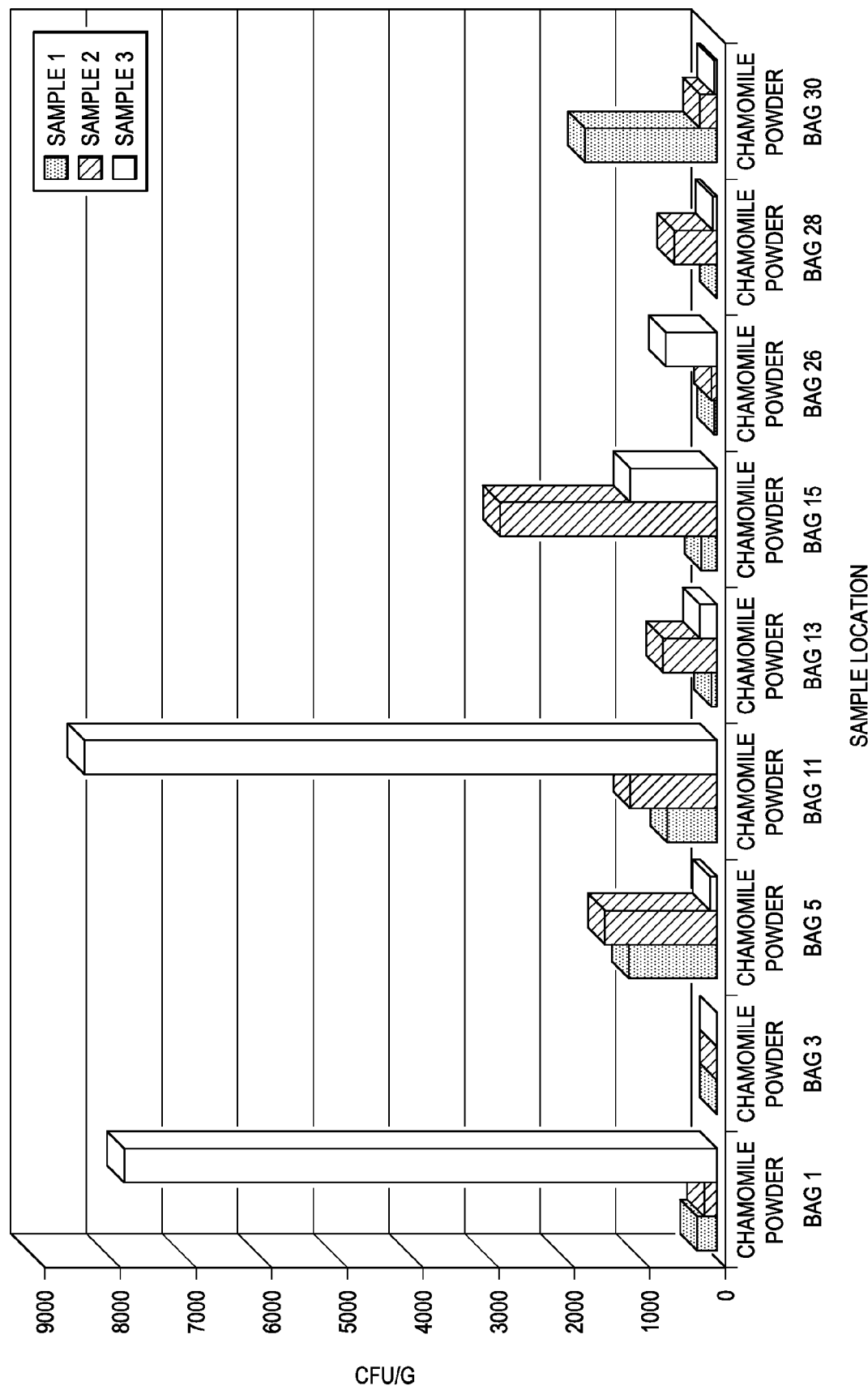

ActiPure™ - RUN # C156
12/7/10 MICRO TESTING

| CART 1 | | INITIAL MICRO | | POST ActiPure™ MICRO | | | ALL SAMPLES | LOG REDUCTION |
|---|---|---|---|---|---|---|---|---|
| | | APC | YEAST/ MOLD | SAMPLE 1 APC | SAMPLE 2 APC | SAMPLE 3 APC | YEAST/ MOLD | |
| BAG 1 | CHAMOMILE POWDER | 5,148,000 | 690 | 60 | 1670 | 280 | <10 | 4 |
| BAG 3 | CHAMOMILE POWDER | 5,148,000 | 690 | 80 | 830 | 10 | <10 | 4 |
| BAG 5 | CHAMOMILE POWDER | 5,148,000 | 690 | 6240 | 8320 | 580 | <10 | 3 |
| BAG 11 | NOPAL POWDER | 400,000 | 190 | 60 | 30 | <10 | <10 | 4 |
| BAG 13 | NOPAL POWDER | 400,000 | 190 | 10 | <10 | <10 | <10 | 4 |
| BAG 15 | NOPAL POWDER | 400,000 | 190 | 20 | <10 | <10 | <10 | 4 |
| BAG 26 | DAMIANA POWDER | 103,000 | 410 | 30 | 440 | 20 | <10 | 3 |
| BAG 28 | YUCCA ROOT POWDER | 29,000,000 | 10 | 32240 | 6240 | 2680 | <10 | 2 |
| BAG 30 | WILD YAM POWDER | 2,392,000 | 470 | 13000 | 45240 | 790 | <10 | 2 |

FIG. 25A

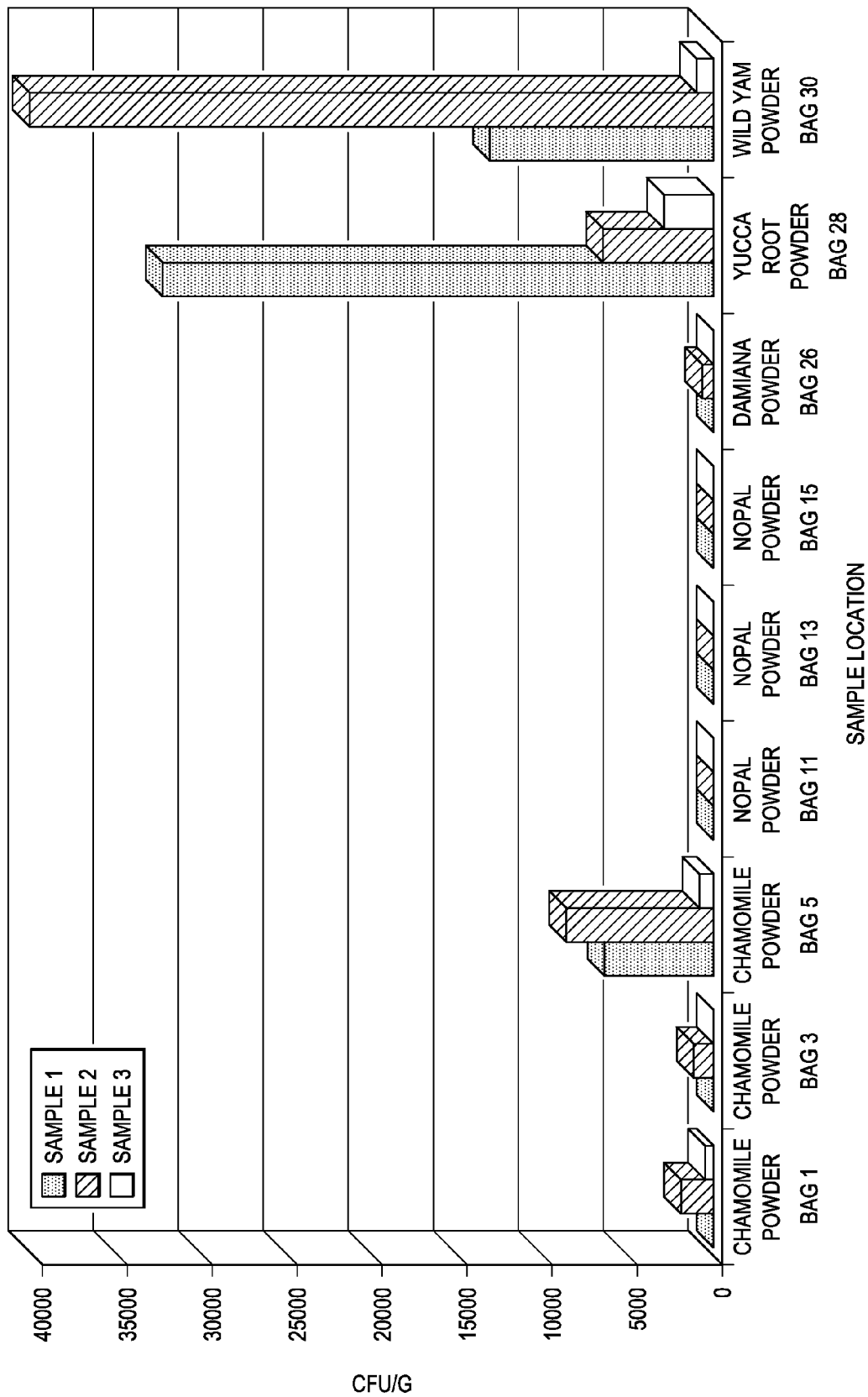

ActiPure™ - RUN # C156
12/7/10 MICRO TESTING

| CART 2 | INITIAL MICRO | | POST ActiPure™ MICRO | | | | |
|---|---|---|---|---|---|---|---|
| | | | SAMPLE 1 | SAMPLE 2 | SAMPLE 3 | ALL SAMPLES | LOG REDUCTION |
| | APC | YEAST/MOLD | APC | APC | APC | YEAST/MOLD | |
| BAG 1 | CHAMOMILE POWDER | 5,148,000 | 690 | 210 | 110 | 7800 | <10 | 3 |
| BAG 3 | CHAMOMILE POWDER | 5,148,000 | 690 | 20 | 20 | 10 | <10 | 5 |
| BAG 5 | CHAMOMILE POWDER | 5,148,000 | 690 | 1110 | 1430 | 60 | <10 | 3 |
| BAG 11 | CHAMOMILE POWDER | 5,148,000 | 690 | 620 | 1100 | 8320 | <10 | 3 |
| BAG 13 | CHAMOMILE POWDER | 5,148,000 | 690 | 40 | 680 | 210 | <10 | 4 |
| BAG 15 | CHAMOMILE POWDER | 5,148,000 | 690 | 190 | 2840 | 1090 | <10 | 3 |
| BAG 26 | CHAMOMILE POWDER | 5,148,000 | 690 | 20 | 40 | 650 | <10 | 4 |
| BAG 28 | CHAMOMILE POWDER | 5,148,000 | 690 | <10 | 550 | 40 | <10 | 4 |
| BAG 30 | CHAMOMILE POWDER | 5,148,000 | 690 | 1720 | 220 | 30 | <10 | 4 |

FIG. 26A

APPARATUS AND METHOD FOR STEAM DISINFECTION OF A POWDER

CROSS-REFERENCE TO RELATED APPLICATIONS

This application claims priority based on U.S. Provisional Application No. 61/494,019, filed Jun. 7, 2012. The contents of each of which is incorporated by reference in its entirety.

TECHNICAL FIELD OF THE INVENTION

The present invention relates in general to the field of sterilization, specifically to an apparatus and method of making and using vacuum and steam for the disinfection of natural products including plant materials and powders in need of sterilization before they can be used by manufacturers and/or consumers.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Without limiting the scope of the invention, its background is described in connection with a sterilization apparatus and method of sterilization of powders.

For example, U.S. Pat. No. 7,895,938 discloses an apparatus and method for steam disinfection of a liquid dispensing machine and a method of using the apparatus. This is achieved by injecting steam into a drained dispenser machine equipped with a cover having a safety valve that matches the top of the dispenser to provide sealing. The steam is generated by a steam generator physically integrated with the new liquid dispenser machine. The steam circulates through the fluid compartment of the liquid dispenser and continues through its conduits and exits at the taps which are held open by a stepped boss. The sanitizing period can be adjusted and controlled.

For example, U.S. Pat. No. 7,892,483 discloses a sterilization process for steroid compositions, in which the steroid is heat treated in the form of a wet mass comprising the steroid, water and an excipient.

For example, U.S. Pat. No. 7,858,028 discloses a pasteurizing or sterilizing process and relates to a method for preparing a product having a low content of microorganisms by using steam. The method can be used to pasteurize or sterilize a product, while retaining the activity of one or more active substances that may be present in the product, and relates to a method wherein a product is dried with air.

BRIEF SUMMARY OF THE INVENTION

The present invention provides a process for sterilization of natural products without negatively effecting the properties of the final product by providing one or more samples comprising one or more natural products for sterilization before they can be used by manufacturers and/or consumers; placing the one or more samples in a steam permeable container; placing the steam permeable container in a sterilization chamber; heating the sterilization chamber to a predetermined temperature; controlling the predetermined temperature; pressurizing the sterilization chamber to a predetermined pressure; controlling the predetermined pressure; supplying an amount of steam to the sterilization chamber; and controlling an application time for the heating, the pressurizing and the supplying the amount of steam to achieve at least partial sterilization of the one or more samples.

The present invention provides dry steam sterilized natural product produced by providing one or more samples comprising one or more natural products for sterilization before they can be used by manufacturers and/or consumers; placing the one or more samples in a steam permeable container; placing the steam permeable container in a sterilization chamber; heating the sterilization chamber to a predetermined temperature; controlling the predetermined temperature; pressurizing the sterilization chamber to a predetermined pressure; controlling the predetermined pressure; supplying an amount of steam to the sterilization chamber; and controlling an application time for the heating, the pressurizing and the supplying the amount of steam to achieve at least partial sterilization of the one or more samples.

The present invention provides a system for the sterilization of natural products without negatively effecting the properties of the system having a sterilization chamber; a sample area within the sterilization chamber to hold one or more steam permeable containers; a heater source connected to the sterilization chamber for heating the sterilization chamber to a predetermined temperature; a heater control unit connected to the heater source for controlling the predetermined temperature; a pressure source connected to the sterilization chamber for pressurizing the sterilization chamber to a predetermined pressure; a pressure control unit connected to the pressure source for controlling the predetermined pressure; a steam aperture for supplying steam to the sterilization chamber; a steam control unit connected to the temperature and duration of the steam; and an interface connected to the heater control unit, pressure control unit, and steam control unit.

BRIEF DESCRIPTION OF THE DRAWINGS

For a more complete understanding of the features and advantages of the present invention, reference is now made to the detailed description of the invention along with the accompanying figures and in which:

FIG. 2 illustrates a graph of the vacuum and temperature profile for the steam sterilization cycle.

FIG. 4 is a table of the weights of the samples.

FIGS. 5, 6 and 7 are graphs of the temperature as a function of time for the samples.

FIGS. 8a and 8b are tables of the results from the sterilization of the samples.

FIGS. 9 and 10 are graphs of the results from the sterilization of the samples.

FIG. 12 is a table of the weights of the samples.

FIGS. 13 and 14 are graphs of the temperature as a function of time for the samples.

FIGS. 15a and 16a are tables of the results from the sterilization of the samples and FIGS. 15b and 16b are graphs of the results from the sterilization of the samples.

FIGS. 18-19 are tables of the weights of the samples.

FIGS. 20, 21 and 22 are graphs of the temperature as a function of time for the samples.

FIGS. 23 and 24 are graphs of the APC Micro test results showing cfu/g as a function of samples location.

FIGS. 25a and 26a are tables of the weights of the samples and FIGS. 25b and 26b are graphs of the APC Micro test results showing cfu/g as a function of samples location.

DETAILED DESCRIPTION OF THE INVENTION

Figure 1A:
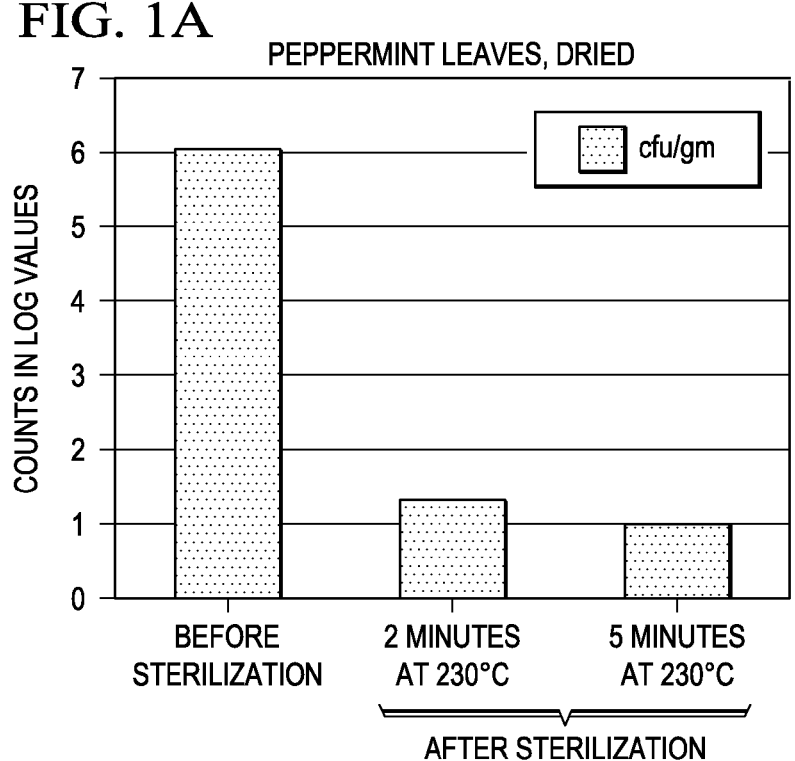
FIGS. 1a and 1b are graphs that illustrate the plate count testing as a function of time.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention may be used to process many natural products including plant materials and powders in need of sterilization before they can be used by manufacturers and/or consumers. The current techniques (e.g., Gamma Radiation, Ethylene Oxide, Ozone, and Ultra Violet Light) used in the industry result in a negative environmental effect, while other treatments introduce residual components into the samples that are carried through the process and provide a negative effect on the properties of the final product. The present invention provides a dry steam sterilization process that does not harm the product, leave residual chemicals, or damage the environment. The present invention provides a combination of elevated temperature, dry steam and vacuum (e.g., negative pressure) to reduce the bioburden. The present invention provides 1, 2, 3, 4, 5, 6, 7, 8, 9, 10, 15, 20, 25, 50, 100 or more (incremental variations thereof) cycles to inactive thermo resistant composition, e.g., thermo resistant spores.

The present invention provides methods and apparatus to produce products sterilized with superheated steam instead of dry air. In one embodiment of a substantially closed system, the superheated steam is recirculated. The part of the steam that condenses during the process will generally be discharged from the device. The superheated steam is passed through the drying chamber and ensures that water evaporates from the product. After leaving the drying chamber, the steam including the steam coming from the product can again be compressed and heated to the desired degree of superheating, and the resulting superheated steam can be returned to the drying chamber. Consequently, the required drying energy is much lower than when conventionally drying with dry air, which cannot be reused so easily. The conditions of drying are selected subject to the product. Those skilled in the art are deemed to reach a suitable optimization on the basis of their normal expert knowledge. In most of the cases, the temperature will range between 150 and 500° C.

It may be clear that the quality of the injected steam must be in accordance with the required quality of the product to be dried. For example, the steam drying of a food product requires that the injected steam be of food grade, and therefore in essence free from mineral oil, moisture droplets, microorganisms, and dirt.

The steam drying according to the invention has the additional advantage that because of the fact that steam is already introduced into the mixing chamber of the nozzle, atomization and pasteurization or sterilization takes place simultaneously, and in a substantially closed system the excess steam can be reused for atomization. Optionally, a product partially dried through drying can be redried to a lower moisture content in a conventional manner, such as, for instance, with a fluid bed-drying device.

Moreover, it has turned out that in a powder dried according to the invention undesired organoleptic changes have been hardly effected, if effected at all, and that a powder dried according to the invention has sufficient solubility for various applications. A method according to the invention is thus suitable for preparing a product consumable without health risks, optionally after reconstitution in a suitable liquid.

Furthermore, the present invention can be used for the manufacture of products or other powdered products that, besides heat-sensitive components, also contain other ingredients in which germs are killed and the activity of heat-sensitive substances, if present, can be retained. It has turned out that such a sterilized and optionally dried product prepared according to the present invention has a suitable microbiological quality. It has also been found after evaluation of a product that during drying according to the invention much fewer undesired reactions, such as oxidation, reduction, irreversible denaturation, and the like, take place than when using conventional techniques. The invention will now be illustrated further with reference to some examples.

The steam treatment apparatus according to the present invention provides a rapid temperature rise by subjecting powders to dry steam at a partial pressure less than about 760 mm Hg. The steam is saturated, and thus the temperature of the steam is held at a desired final temperature. The steam temperature-pressure relationships are well known, and need not be reviewed herein.

The steam in one preferred embodiment is provided by a steam generator, which boils, for example, potable or distilled water. This water is degassed prior to use, so that the steam contains few impurities and almost no non-condensing impurities. The steam generator may be at any temperature above the final temperature, e.g., 150 C, as the thermal treatment of the droplets derives mainly from the latent heat of vaporization of the droplets, and very little from the absolute temperature of the steam. Preferably, the steam is saturated, which will define its temperature in a given atmosphere.

Thus, the mass flow rate of the saturated steam entering into the treatment system (in relation to the product flow rate and any withdrawal of steam or external heat transfer), controls the process treatment temperature. In the case of an over-pressure steam generator, the mass flow rate is restricted to prevent the treated droplets from reaching too high a temperature, or supersaturation conditions.

The steam is derived from a boiler. Tight control of temperature may require a high temperature boiler with a control valve near the reactor vessel. In other words, in order to ensure adequate flow of steam into the reactor, an excess capacity should be available from the boiler. Control is effected near the reactor, to avoid time response delays or oscillation. The water in the boiler is preferably degassed to eliminate non-condensable components. The boiler may have a superheater at its outlet, to heat the steam over a condensation equilibrium level.

The steam is injected into the reactor vessel through a number of steam injection ports, spaced within the chamber, so that the region distant from the fluid injection port maintains a relatively constant water vapor pressure. The walls of the reactor vessel should be maintained at least at or slightly above the final operating temperature, to avoid condensation of steam on the wall and unnecessary product dilution. This may be accomplished by any suitable heating system.

One embodiment of the present invention provides a dry steam sterilization process to produce a clean sterilization process and apparatus that is natural and organic with no harm to the product, no residual chemicals and no damage to the environment. The product is controlled and monitored for consistent, homogenous treatment results and preserves product integrity and optimal sensory properties to the product with little or no aesthetic changes. The present invention can use a wide range of products including herbs, botanicals and spices, to free-flowing powders can be treated with this process.

The present invention includes devices and methods that reduce (e.g., >4 log reduction) the presence of TPC, yeasts and molds, with little or no aesthetic changes while preserving product integrity and optimal sensory properties. In addition, the present invention can accommodate numerous samples that are similar or different and allows each individual sample to be controlled and monitored to ensure consistent and homogenous treatment results.

The present invention provides a dry steam sterilization process. The samples are placed in a sample container. The sample container is placed into a sterilization chamber to provide dry steam and exert both temperature and pressure on the sample. The sterilization chamber undergoes a controlled dry steam cycle for a predetermined temperature at a predetermined pressure based on the sample, batch size, product density. For example, the controlled dry steam cycle may be for 5-300 minutes at between 100 to 300° F. at 0-15 psi. One specific embodiment has a controlled dry steam cycle for 15-25 minutes at 150° F. at 5 psi. Sterilization chambers can be formed in any particular dimensions to accommodate the sample containers. The sterilization chamber is cooled to cool the sample container before transfer to a clean room. The sample container can then be prepared for use, storage or shipping.

One embodiment includes placing the samples on a rack having numerous shelves to separate and hold the samples. The rack is then placed into the sterilization chamber. In some instances the rack is a rolling cart that can be rolled into the sterilization chamber. The samples are dried at a temperature of between 185 and 230° F. for between 8 and 12 hours. The sterilization chamber then receives a flush with steam for about 1 hour. The sterilization chamber was held at 220° F. for 45 minutes and a vacuum of about 3 inches of Hg applied to the sterilization chamber for about 30 minutes. The sterilization chamber was then vented to the atmosphere and allowed to cool.

One sample of 10 kg of Peppermint Leaves and Walnut shells were placed into bags and positioned in the sterilization chamber for sterilization using the dry steam vacuum of the present invention and showed a greater than 5 log reduction for both gram negative and gram positive spore-forming bacteria after 2 and 5 minutes of treatment.

More general parameters include samples that are dried by heating the sterilization chamber to a temperature of between 150 and 350° F. for between 1 and 24 hours. The sterilization chamber then receives a flush with steam for between 1 and 24 hours. The sterilization chamber was held at between 150 and 350° F. for between 0 and 24 hour and a vacuum of about from about −35 psi to 35 psi applied to the sterilization chamber for about 30 minutes. The sterilization chamber was then vented to the atmosphere and allowed to cool.

Aerobic Plate Count Testing was used to indicate the level of microorganisms in the raw material and the finished product. Bacteria (BBL 11764) was incubated at 33-35° C. for 48-72 hours with tryptic soy agar with lecithin and TWEEN. Mold (BBL 11550) was incubated at 20-25° C. for 5 days with potato dextrose agar. Diluent (BBL 12201) was used with tat broth.

Figure 1B:
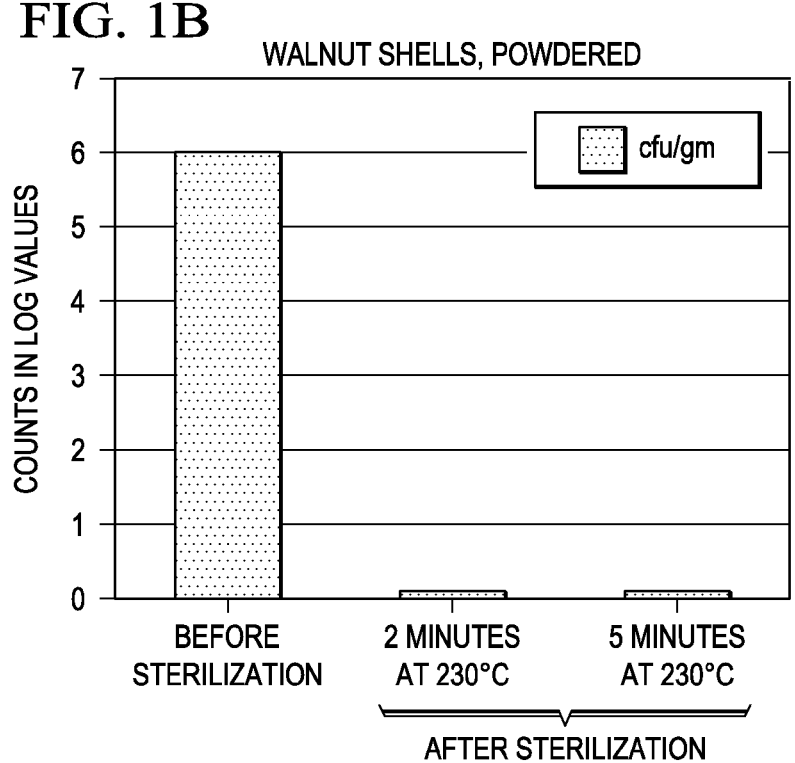

FIGS. 1a and 1b are graphs that illustrate the plate count testing (cfu/gm) as a function of time starting before sterilization and including at 2 minutes at 230° C. and 5 minutes at 230° C.

FIG. 2 illustrates a graph of the vacuum and temperature profile for the steam sterilization cycle as a function of time for rosemary leaves, walnut shells, comfrey leaves, licorice root, rosemary cube, horsetail leaf, and calendula flower.

Figure 3:
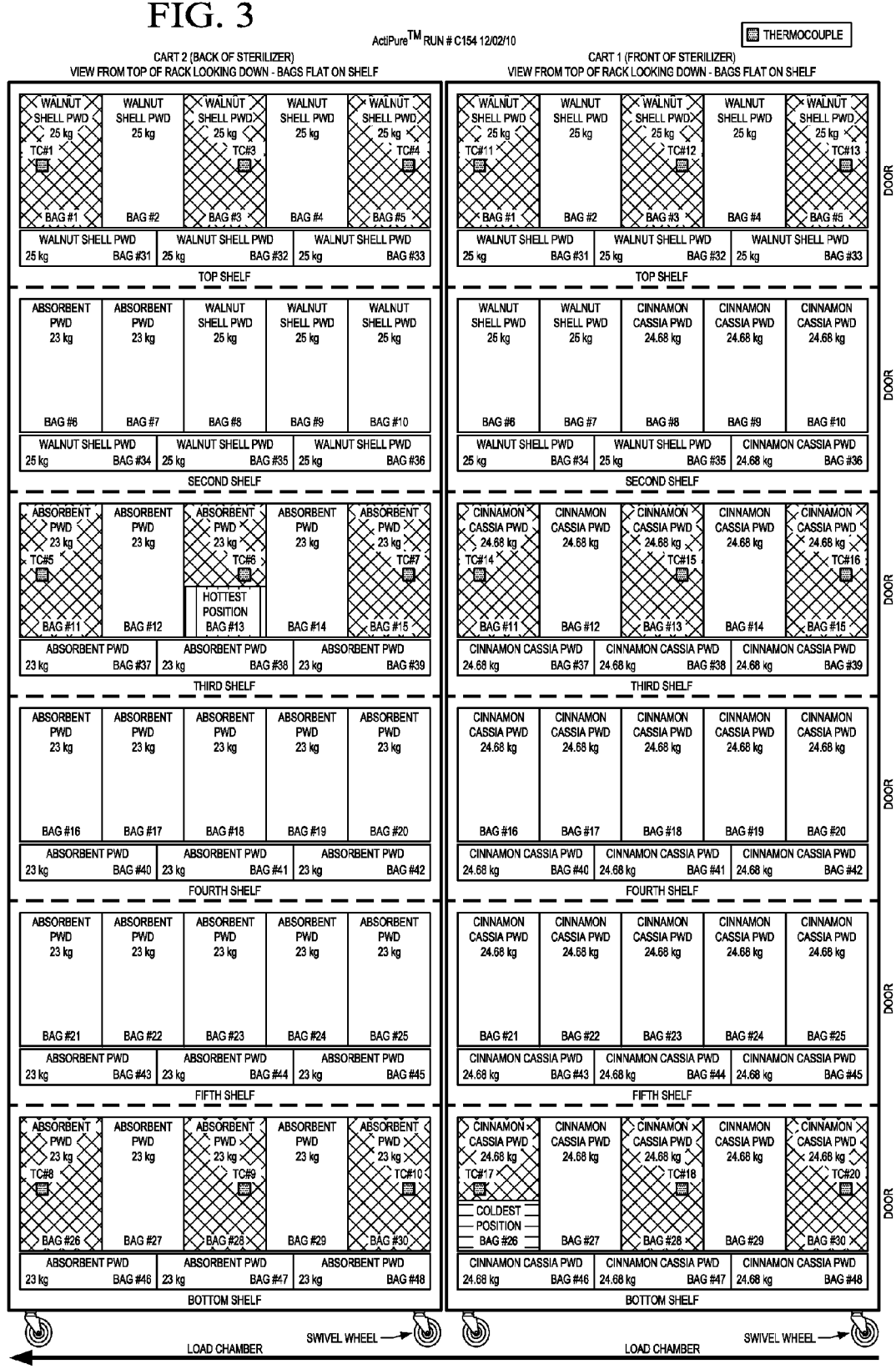
FIG. 3 is an image and location of numerous samples distributed on six shelves on two racks.

FIG. 3 is an image of another embodiment C154 of the present invention that provides numerous samples distributed on six shelves on two racks. The samples are distributed flat on the shelf with an adsorbent powder placed below the samples. The samples are placed on cart 1 and cart 2 and placed into the sterilization chamber. The sterilization chamber was pre-heated. At 4 hours 30 minutes the steam and air pressure were turned off and the vessel was allowed to sit overnight. The temperature slowly decreased to 160-190° F. The next morning, the steam and air pressure were turned on and the vessel heated another 6 hours until the product was above 180° F. Eighteen thermocouples (not shown) were placed in bags (not shown) throughout the product. During the heat up process four locations (not shown) indicated thermocouple noise and are considered abnormal readings: thermocouple #4 (not shown) in Bag R2-5 (not shown); thermocouple #8 (not shown) in Bag R2-26 (not shown); thermocouple #9 (not shown) in Bag R2-26 (not shown) and thermocouple #16 (not shown) in Bag R1-15 (not shown). The remaining fourteen thermocouples (not shown) appeared to function normally. The samples (not shown) were treated with a 15-minute exposure, with eighteen thermocouples (not shown) placed in bags (not shown) throughout the product (not shown). During the run cycle, one location (not shown) indicated thermocouple noise and is considered an abnormal reading: thermocouple #16 (not shown) in Bag R1-15 (not shown) but the remaining seventeen thermocouples (not shown) appeared to function normally. During exposure, the eighteen thermocouples (not shown) temperatures ranged from 220°-253.44° F. At the end of the run cycle, thermocouple #1 in Bag R2-1 showed an abnormal increase in temperature after the cycle.

FIG. 4 is a table of the weights of the samples. The coldest run position was located in rack 1 (not shown), Bag 26 (not shown) (thermocouple #17) of FIG. 3 at 40 minutes. The hottest run position was in rack 2, bag 13 (thermocouple #6 (not shown)). The pre-sample micro read was APC 77,000 cfu/g and Yeast/Mold <10 cfu/g. The post-process micro read was APC <10 cfu/g and Yeast/Mold <10 cfu/g. The disposition was 5 log reduction. The samples (not shown) underwent post processing by removing 2 oz., were taken from eighteen of the 96 bags (not shown) placed throughout representative of the vessel area (not shown). Sampling locations are indicated in yellow on the cart mapping diagram of FIG. 3. Each bag was sampled in three locations: left, middle and right, with one sample location corresponding with the thermocouple placement in the bag (not shown). A total of 54 samples (not shown) were gathered and tested for the run.

FIGS. 5-7 are graphs of the temperature as a function of time for the samples.

FIGS. 8a and 8b are tables of the results from the sterilization of the samples.

FIGS. 9 and 10 are graphs of the results from the sterilization of the samples. The average percent loss per product after grind has been determined to be on average <1%. The sterilization results are shown below:

| Bag # | Product | |
|---|---|---|
| | Cinnamon APC | Cassia Powder Yeast/Mold |
| 1 | 20 | <10 |
| 9 | <10 | <10 |
| 18 | <10 | <10 |
| 21 | <10 | <10 |
| 29 | <10 | <10 |

Figure 11:
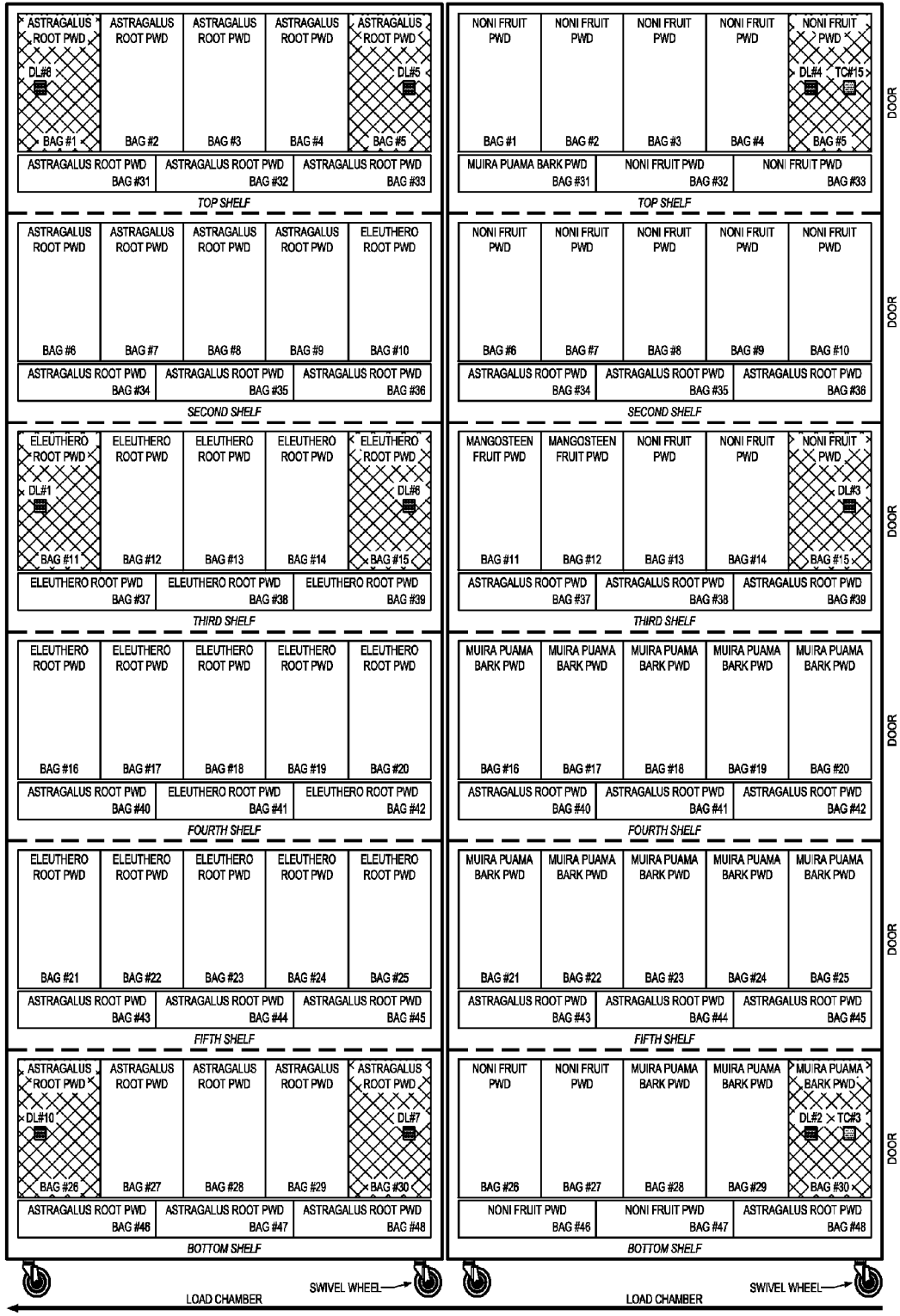
FIG. 11 is an image of numerous samples distributed on six shelves on two racks.

FIG. 11 is an image of another embodiment of the present invention that provides numerous samples distributed on six shelves on two racks. The samples are distributed flat on the shelf with an adsorbent powder placed below the samples. The samples are placed on cart 1 and cart 2 and placed into the sterilization chamber. The sterilization chamber was pre-heated. At 4 hours 30 minutes the steam and air pressure were turned off and the vessel was allowed to sit overnight. The temperature slowly decreased to 160-190° F. The next morning, the steam and air pressure were turned on and the vessel heated another 6 hours until the product was above 180° F. The samples were treated with a 15-minute exposure.

FIG. 12 is a table of the weights of the samples. The post-process micro read was APC <10 cfu/g and Yeast/Mold <10 cfu/g.

FIGS. 13 and 14 are graphs of the temperature as a function of time for the samples.

Figures 15A, 15B:
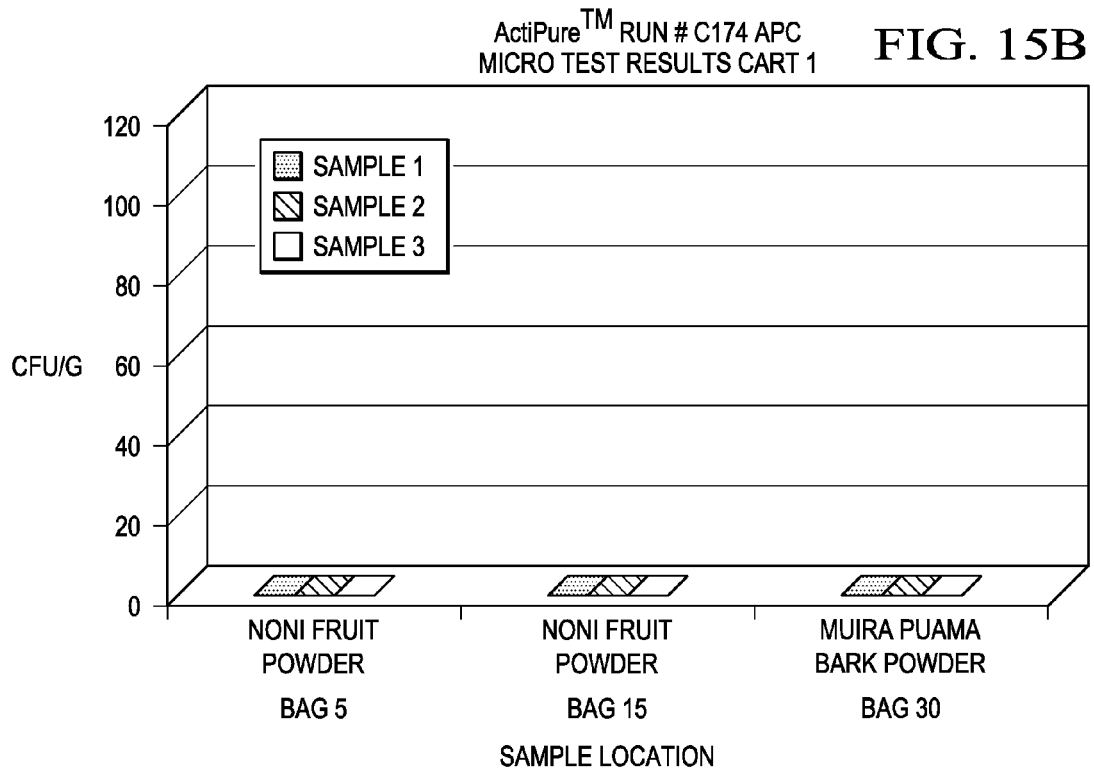
Figure 16B:
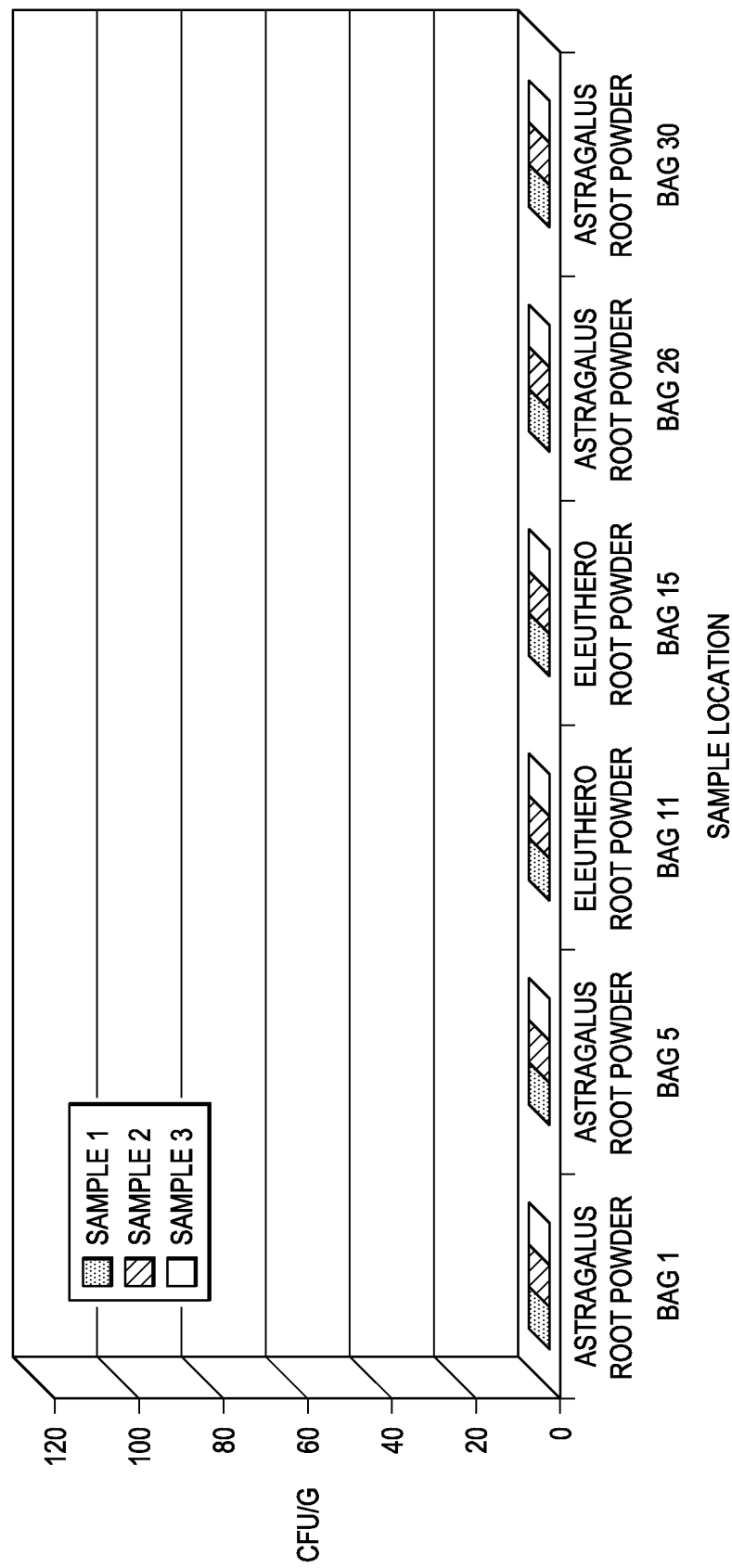

FIGS. 15a and 16a are tables of the results from the sterilization of the samples and FIGS. 15b and 16b are graphs of the results from the sterilization of the samples.

Figure 17:
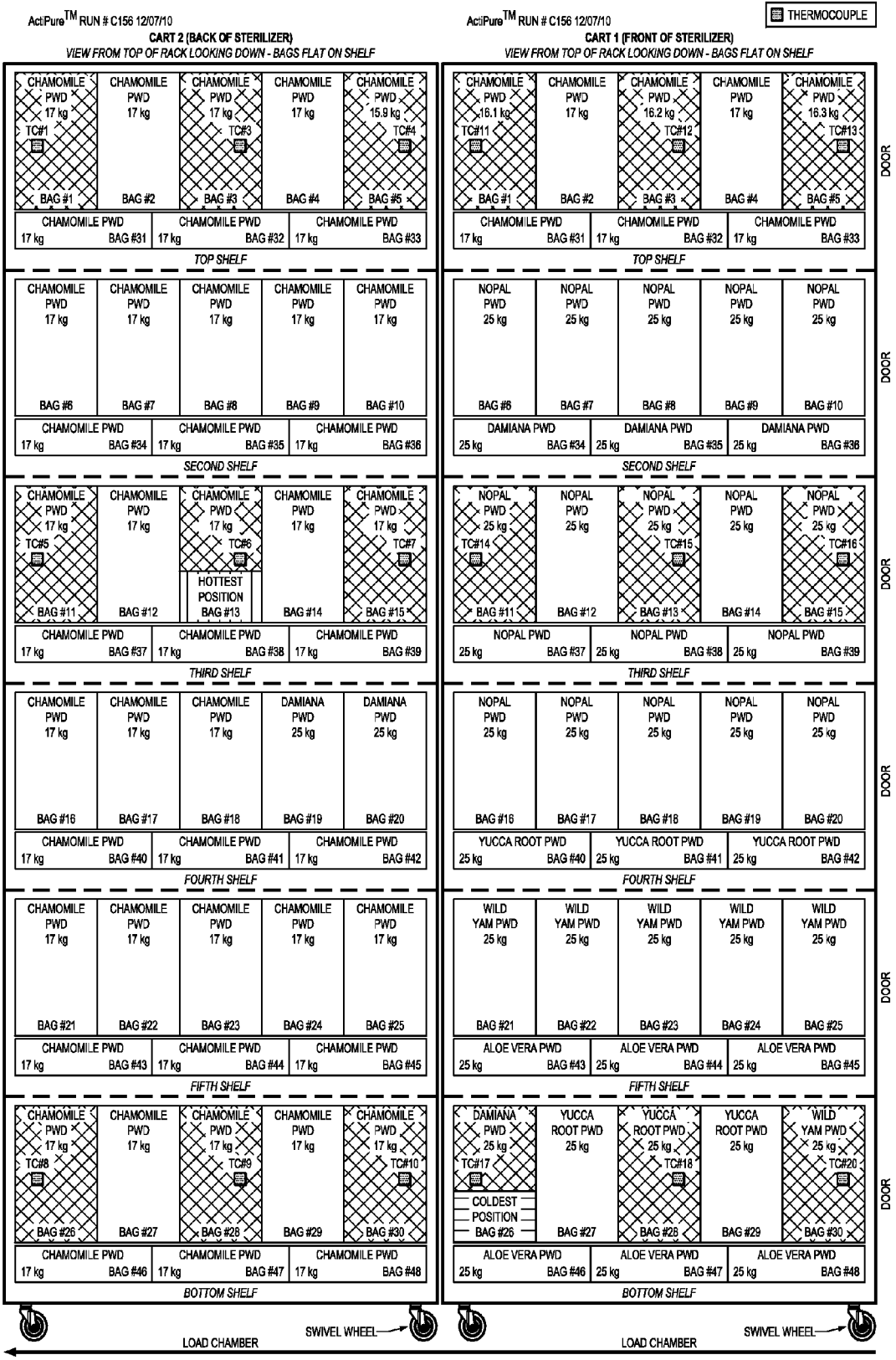
FIG. 17 is an image of numerous samples distributed on six shelves on two racks.

FIG. 17 is an image of another embodiment C156 of the present invention that provides numerous samples distributed on six shelves on two racks. The samples are distributed flat on the shelf with an adsorbent powder placed below the samples. The samples are placed on cart 1 and cart 2 and placed into the sterilization chamber. The sterilization chamber was pre-heated with the jacket temperature set at 200° F. and allowed vessel to sit overnight, approximately 15 hours. The next morning the jacket temperature was increased to 230° F., and in approximately one hour all product reached 180° F. Eighteen (18) thermocouples were placed in bags throughout the product. During the heat up process two (2) locations indicated thermocouple noise and are considered abnormal readings: thermocouple #18 in Bag R1-28 and thermocouple #21 in Bag R1-3. The remaining sixteen (16) thermocouples appeared to function normally. The samples were treated with a 15-minute exposure, with eighteen (18) thermocouples placed in bags throughout the product. During the run cycle, three (3) locations indicated thermocouple noise and is considered an abnormal reading: thermocouple #8 in Bag R2-26; thermocouple #16 in Bag R1-15 and thermocouple #14 in Bag R1-11 but the remaining fifteen (15) thermocouples appeared to function normally. During exposure, the eighteen (18) thermocouples temperatures ranged from 220°-249.04° F.

FIGS. 18-19 are tables of the weights of the samples: The coldest run position was in rack 1, Bag 26 (thermocouple #17) at 36 minutes. The hottest run position was in rack 2, bag 13 (thermocouple #15). The pre-sample micro read was APC 148,000 cfu/g and Yeast/Mold N/A. The post-process micro read is listed below:

| | | Post Actipure Micro | | | | |
|---|---|---|---|---|---|---|
| Cart 1 | | Sample 1 APC | Sample 2 APC | Sample 3 APC | All Samples Yeast/Mold | Log Reduction |
| Bag 1 | Chamomile Powder | 60 | 1670 | 290 | <10 | 4 |
| Bag 3 | Chamomile Powder | 80 | 830 | 10 | <10 | 4 |
| Bag 5 | Chamomile Powder | 6240 | 8320 | 580 | <10 | 3 |
| Bag 11 | Nopal Powder | 60 | 30 | <10 | <10 | 4 |
| Bag 13 | Nopal Powder | 10 | <10 | <10 | <10 | 4 |
| Bag 15 | Nopal Powder | 20 | <10 | <10 | <10 | 4 |
| Bag 26 | Damiana Powder | 30 | 440 | 20 | <10 | 3 |
| Bag 28 | Yucca Root Powder | 32240 | 6240 | 2680 | <10 | 2 |
| Bag 30 | Wild Yarn Powder | 13000 | 45240 | 790 | <10 | 2 |

| | | Post Actipure Micro | | | | |
|---|---|---|---|---|---|---|
| Cart 2 | | Sample 1 APC | Sample 2 APC | Sample 3 APC | All Samples Yeast/Mold | Log Reduction |
| Bag 1 | Chamomile Powder | 210 | 110 | 7800 | <10 | 3 |
| Bag 3 | Chamomile Powder | 20 | 20 | 10 | <10 | 5 |
| Bag 5 | Chamomile Powder | 1110 | 1430 | 60 | <10 | 3 |
| Bag 11 | Chamomile Powder | 620 | 1100 | 8320 | <10 | 3 |
| Bag 13 | Chamomile Powder | 40 | 680 | 210 | <10 | 4 |
| Bag 15 | Chamomile Powder | 190 | 2840 | 1090 | <10 | 3 |
| Bag 26 | Chamomile Powder | 20 | 40 | 650 | <10 | 4 |
| Bag 28 | Chamomile Powder | <10 | 550 | 40 | <10 | 4 |
| Bag 30 | Chamomile Powder | 1720 | 220 | 30 | <10 | 4 |

The disposition was 5 log Reduction. The samples underwent post processing by removing 2 oz., were taken from eighteen (18) of the 96 bags placed throughout representative of the vessel area. Sampling locations are indicated in yellow on the cart mapping diagram. Each bag was sampled in three (3) locations: left, middle and right, with one (1) sample location corresponding with the thermocouple placement in the bag. A total of 54 samples were gathered and tested for the run. The average percent loss per product for the run is as follows:

| Product | % Loss |
| --- | --- |
| *Aloe Vera* Powder | 4% |
| Chamomile Powder | 7% |
| Damiana Powder | 4% |
| Napal Powder | 4% |
| Wild Yam Powder | 5% |
| Yucca Root Powder | 3% |

Figure 21:
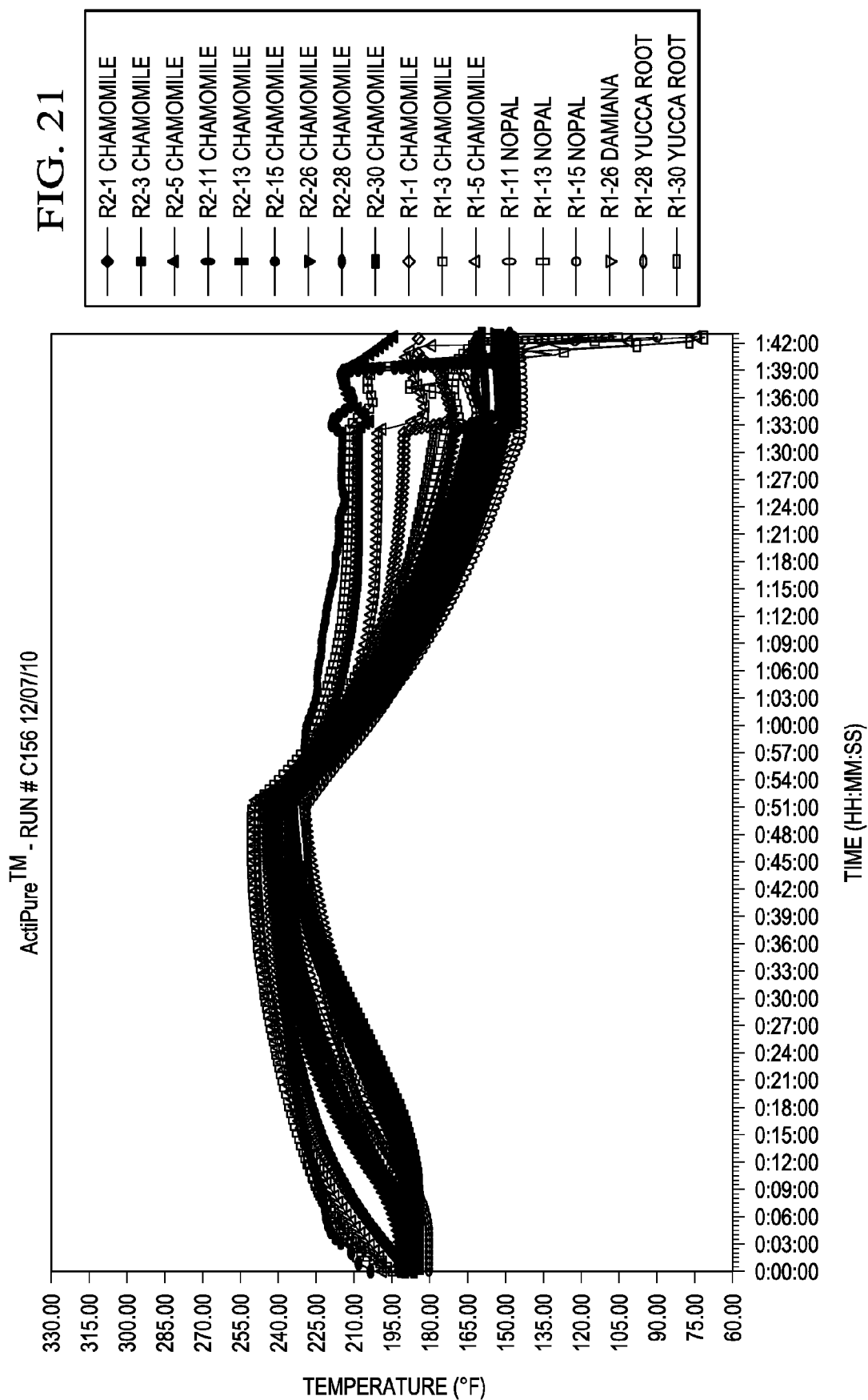
Figure 22:
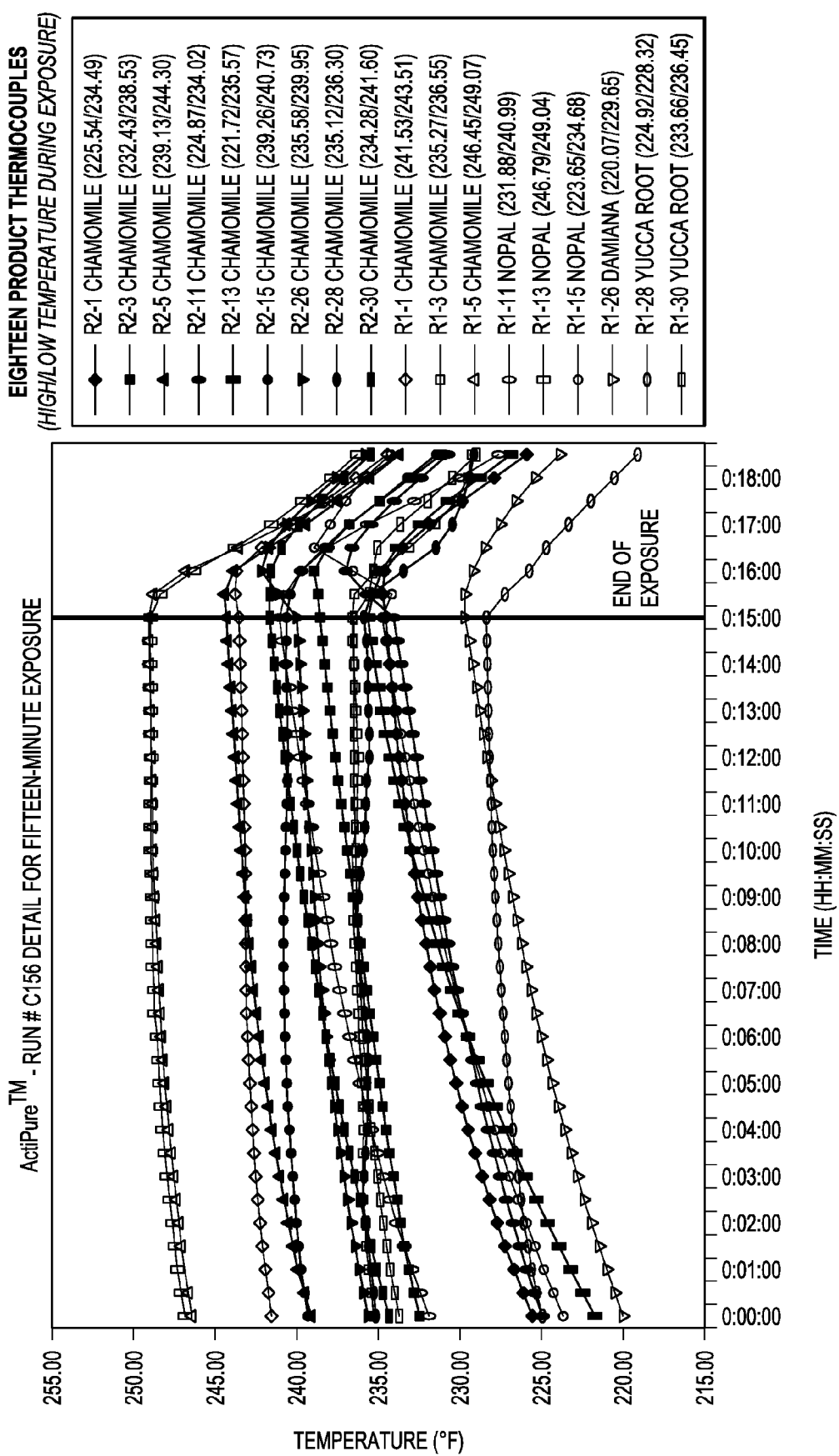
Figure 26B:
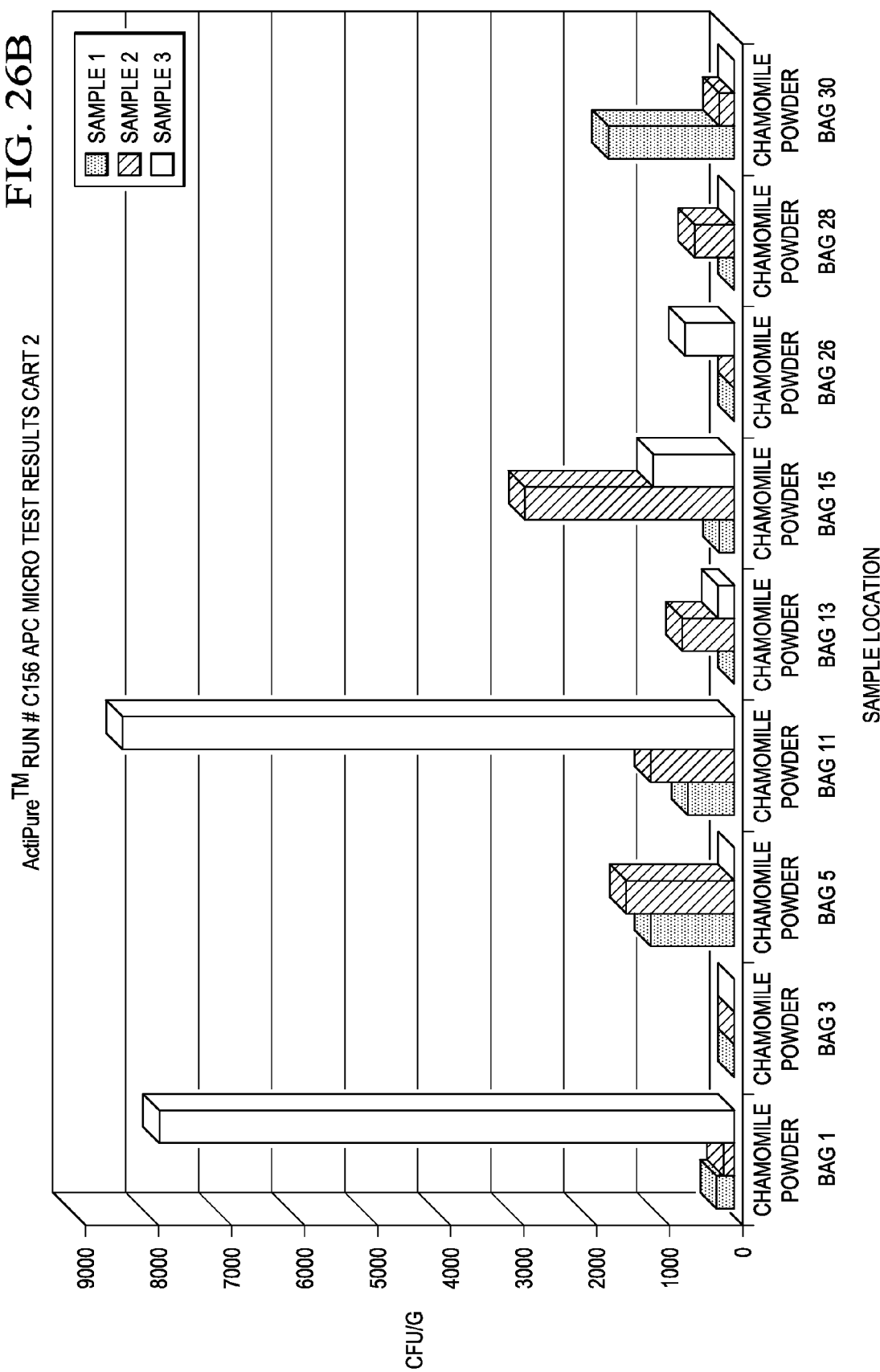

FIGS. 20, 21 and 22 are graphs of the temperature as a function of time for the samples. FIGS. 23 and 24 are graphs of the APC Micro test results showing cfu/g as a function of samples location. FIGS. 25a and 26a are tables of the weights of the samples and FIGS. 25b and 26b are graphs of the APC Micro test results showing cfu/g as a function of samples location.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A process for sterilization of natural products using dry superheated steam without negatively effecting the properties of the final product comprising the steps of:
providing a dry steam sterilization apparatus comprising a sterilization chamber, a steam generator and a steam drying chamber;
providing one or more samples comprising one or more natural products for sterilization before they can be used by manufacturers and/or consumers;
placing the one or more samples in a steam permeable container;
placing the steam permeable container in the sterilization chamber;
heating the sterilization chamber to a predetermined temperature;
controlling the predetermined temperature;
pressurizing the sterilization chamber to a predetermined pressure;
pulling a vacuum for a predetermined length of time and pressure;
controlling the predetermined pressure;
producing a steam supply with the steam generator
superheating the steam supply to produce a superheated steam;
passing the superheated steam through the steam drying chamber to produce a dry superheated steam;
supplying an amount of the superheated dry steam to the sterilization chamber; and
controlling an application time for the heating, the pressurizing and the supplying the amount of the superheated dry steam to achieve at least partial sterilization of the one or more samples.

2. The process of claim 1, further comprising the step of repeating the steps one or more times to achieve the desired level of sterilization of the one or more samples.

3. The process of claim 1, wherein the one or more samples are one or more powders for sterilization before they can be used by manufacturers and/or consumers.

4. The process of claim 1, wherein the predetermined pressure is a negative pressure.

5. The process of claim 1, wherein the predetermined temperature is between 100 to 300° F.

6. The process of claim 1, wherein the predetermined pressure is between 0-15 psi.

7. The process of claim 1, wherein the one or more samples are heated, pressurized, and steamed for between 5-300 minutes.

8. A process for sterilization of natural products using dry superheated steam without negatively effecting the properties of the final product comprising the steps of:
- providing a dry steam sterilization apparatus comprising a sterilization chamber, a steam generator and a steam drying chamber;
- providing one or more natural powder product samples;
- placing the one or more samples in a steam permeable container;
- placing the steam permeable container in the sterilization chamber;
- heating the sterilization chamber to a predetermined temperature;
- controlling the predetermined temperature;
- pressurizing the sterilization chamber to a predetermined pressure;
- pulling a vacuum for a predetermined length of time and at the predetermined pressure;
- controlling the predetermined pressure;
- producing a steam supply with the steam generator
- superheating the steam supply to produce a superheated steam;
- passing the superheated steam through the steam drying chamber to produce a dry superheated steam;
- supplying an amount of the superheated dry steam to the sterilization chamber; and
- controlling an application time for the heating, the pressurizing and the supplying the amount of the superheated dry steam to achieve at least partial sterilization of the one or more samples.

* * * * *